(12) United States Patent
Zhang et al.

(10) Patent No.: US 12,018,038 B2
(45) Date of Patent: Jun. 25, 2024

(54) MAIN GROUP METAL COMPLEX AND ITS PREPARATION METHOD AND USE

(71) Applicant: PEKING UNIVERSITY, Beijing (CN)

(72) Inventors: Junlong Zhang, Beijing (CN); Haoyan Yin, Beijing (CN); Bingwu Wang, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 896 days.

(21) Appl. No.: 16/973,474

(22) PCT Filed: May 9, 2019

(86) PCT No.: PCT/CN2019/086272
§ 371 (c)(1),
(2) Date: Dec. 9, 2020

(87) PCT Pub. No.: WO2019/214691
PCT Pub. Date: Nov. 14, 2019

(65) Prior Publication Data
US 2021/0253603 A1    Aug. 19, 2021

(30) Foreign Application Priority Data

May 11, 2018  (CN) .......................... 201810446199.9
Mar. 29, 2019 (CN) .......................... 201910251385.1

(51) Int. Cl.
| | | |
|---|---|---|
| C07C 407/00 | (2006.01) | |
| A61K 9/00 | (2006.01) | |
| A61P 35/00 | (2006.01) | |
| C07F 5/00 | (2006.01) | |
| C07F 5/06 | (2006.01) | |

(52) U.S. Cl.
CPC ............ *C07F 5/003* (2013.01); *A61K 9/0019* (2013.01); *A61P 35/00* (2018.01); *C07F 5/069* (2013.01)

(58) Field of Classification Search
CPC ........................... C07C 407/00; C07C 407/03
See application file for complete search history.

(56) References Cited

PUBLICATIONS

Cheng et al. A Class of Multi-responsive Colorimetric and Fluorescent pH Probes via Three Different Reaction Mechanisms of Salen Complexes: A Selective and Accurate pH Measurement. Inorganic Chemistry, vol. 55, 9221-9229. (Year: 2016).*
Huang et al. Computational Design of Two-Photon Fluorescent Probes for a Zinc Ion Based on a Salen Ligand. Inorganic Chemistry, vol. 52, 5702-5713. (Year: 2013).*
Kawakami et al. cis-trans Isomerisation of Dimethyltin Bis (Salicylaldehyde)-Ethylenediiminate. Journal of Organometallic Chemistry, vol. 70, 67-77. (Year: 1974).*
Dey et al. Synthesis and characterization of diorganotin (IV) complexes of tetradentate Schiff bases: crystal structure of n-Bu2 (Sn) (Vanophen). Polyhedron 18, 2687-2696. (Year: 1999).*
Aziz et al. Synthesis, spectroscopic, photoluminescence properties and biological evaluation of novel An(II) and Al (III) complexes of NOON tetradentate Schiff bases. Spectrochimica Acta Part A: Molecular and Biomolecular Spectroscopy 97, 388-396. (Year: 2012).*

* cited by examiner

*Primary Examiner* — Sikarl A Witherspoon
(74) *Attorney, Agent, or Firm* — CBM PATENT CONSULTING, LLC

(57) ABSTRACT

The present invention provides a main group metal complex, or pharmaceutically acceptable salt, solvate, non-covalent bond compound or prodrug thereof, which is composed of planar tetradentate Schiff base ligands and p-block main group metal ions. The main group metal complex can be conveniently prepared, and shows high cytotoxicity to a variety of cancer cell lines and has selective killing effect. The pharmaceutical compositions or pharmaceutical preparations prepared from the main group metal complex according to the present invention can be used for treatment of tumors. The main group metal complex also has fluorescent properties and can be used for fluorescent labeling.

9 Claims, 6 Drawing Sheets

MAIN GROUP METAL COMPLEX AND ITS PREPARATION METHOD AND USE

TECHNICAL FIELD

The present invention relates to a main group metal complex with cancer cell killing effect, its preparation method and use in cancer treatment.

BACKGROUND ART

Metal complex based small molecule anticancer drugs are important as a type of chemotherapy drug. Currently, in this field, the studies mostly focus on transition metal complexes based on such as platinum, ruthenium, and gold. Few attentions have been paid on the anticancer characteristics of main group metal complexes.

It has been demonstrated by many studies that main group metal complexes of groups 13, 14 and 15 have medicinal and anticancer activities (Seng, H-L. and E. R. T Tiekink; Main-Group Medicinal Chemistry Including Li and Bi. *Comprehensive Inorganic Chemistry II*, Vol 3. Oxford: Elsevier; 2013, 951-974). Recently, it has been reported that main group metal complexes with cell-killing ability include indium and tin complexes of thiosemicarbazone (Galvan-Hidalgo, J. M.; et al. *J. Organometal. Chem.* 2017, 848, 332-343), gallium trimaltol and tri-8-hydroxyquinoline complex (Gogna, R.; Madan, E.; Keppler, B.; Pati, U.; *Br. J. Pharmacol.*, 2012, 166, 617), and organogermanium buxicin complexes, etc. (Yang F., et al.; *Bioorg. Med. Chem. Lett.*, 2013, 23, 5544). Additionally, it has also been disclosed that gallium corrole complexes have significantly higher photodynamic therapeutic activity than ligands (M. Pribisko, J. Palmer, R. H. Grubbs, H. B. Gray, J. Termini, P. Lim; *PNAS*, 2016, 113(16), E2258).

However, currently, most of the researches on the anticancer ability of main group metal complexes are proceeded by way of in vitro experiments. Although, compared with transition metal complexes such as cisplatin complex, main group metal complexes used as anticancer drugs still have some problems such as limited treatment ways, taking effect slowly and low toxicity, current works also show that they have the potential in the application of anticancer drugs.

It has been demonstrated by more and more evidences that the medicinal and anticancer activities of the main group metal complexes of groups 13, 14 and 15 would be affected by the species and structures of main group metals and their ligands bonded thereto. Therefore, the selection of suitable main group metals and their ligands is of great significance for improving the medicinal and anticancer activities of main group metal complexes.

SUMMARY OF THE INVENTION

In order to overcome the above-mentioned problems, the inventor of the present invention have made great efforts and found that: a salicylaldehyde or substituted salicylaldehyde, a diamine precursor and a main group metal can react to yield a main group metal complex with anti-tumor effect, which further has fluorescent properties and thus can be used as an optical label as well.

Therefore, according to the present invention, it is to provide:

in a first aspect, a main group metal complex having the structure represented by Formula I or Formula II as below, or pharmaceutically acceptable salt, solvate, non-covalent bond compound or prodrug thereof,

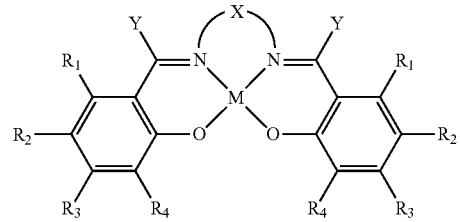

Formula I

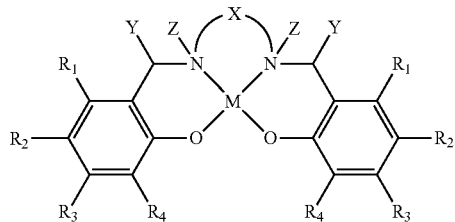

Formula II which, including its cation, is composed of planar tetradentate Schiff base ligands and p-block main group metal ions, wherein, M represents the p-block main group metal;

X represents a diamine residue, and nitrogen atoms on each side of its imine bond are connected by substituted or unsubstituted $C_{1-12}$ alkyl or $C_{2-12}$ alkenyl, or X exists as ortho-substituents of a substituted or unsubstituted aryl or heterocyclic aryl;

Y is hydrogen, $C_{1-12}$ alkyl, halogen, halogen-substituted alkyl, cyano, amino, carbonyl, $C_{1-12}$ alkoxy or substituted amino;

Z is hydrogen, $C_{1-12}$ alkyl, halogen, nitro, hydroxyl, mercapto or carboxyl;

$R_1$, $R_2$, $R_3$ and $R_4$ are substituents on the benzene ring of the corresponding ligand, and are each independently selected from hydrogen, halogen, nitro, hydroxyl, mercapto, carboxyl, amino, cyano, $C_{1-12}$ alkyl, $C_{2-12}$ alkenyl, $C_{2-12}$ alkynyl, $C_{1-8}$ alkoxy, $C_{2-8}$ alkenyloxy, $C_{2-8}$ alkynyloxy, $C_{1-8}$ alkylthio, $C_{3-8}$ heterocyclyl, aryl, $C_{1-8}$ alkanoyl, $C_{1-8}$ alkamido, $C_{1-8}$ alkylsulfonyl, arylsulfonyl, $C_{1-12}$ alkyl substituted amino or halogen substituted $C_1$-12 alkyl, or two adjacent substituents among $R_1$, $R_2$, $R_3$ and $R_4$ ($R_1$ and $R_2$, $R_2$ and $R_3$ and/or $R_3$ and $R_4$) may form a ring;

in a second aspect, a method for preparing the main group metal complex as disclosed above, in which a salicylaldehyde or substituted salicylaldehyde represented by Formula V, a diamine precursor represented by Formula VI, and a main group metal salt MD are added in an organic solvent L, and the reaction is carried out at a temperature ranging from 50 to 150° C. for 12 to 24 h, and then the product represented by Formula III is obtained:

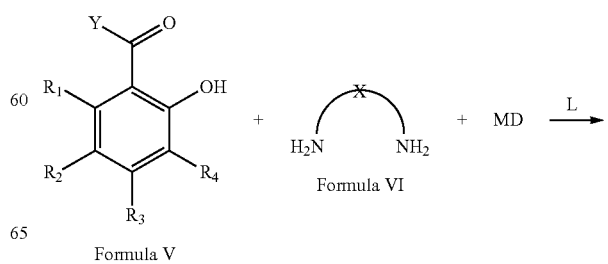

Formula V    Formula VI

-continued

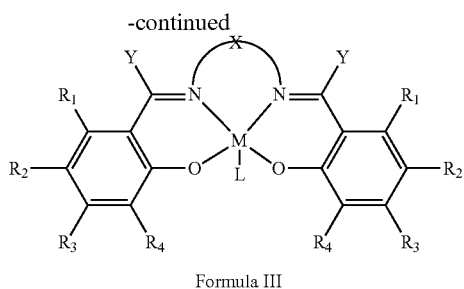

Formula III wherein the product represented by Formula IV can be produced according to the following reaction scheme, in which a ligand represented by Formula VII and a main group metal salt MD are added in an organic solvent L, and the reaction is carried out at a temperature ranging from 50 to 150° C. for 12 to 24 h, and then the target complex molecule is obtained in one step:

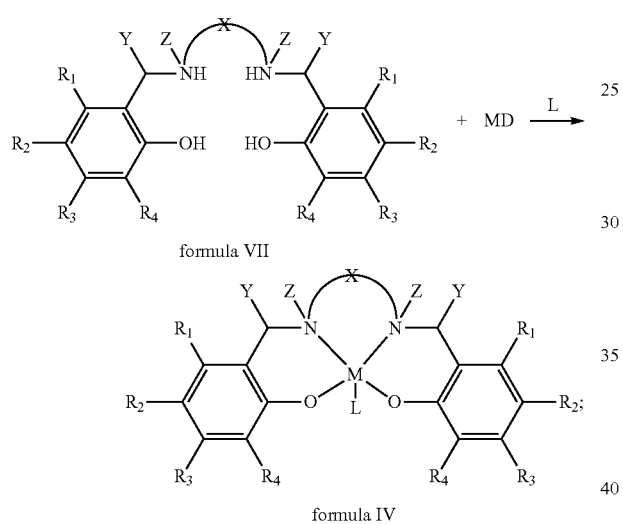

in a third aspect, a pharmaceutical composition using the above main group metal complex as an active ingredient, which further comprises pharmaceutically acceptable excipient;

in a fourth aspect, a pharmaceutical preparation containing the above main group metal complex, which can be administrated through gastrointestinal tract or by injection, wherein the preparations administrated through gastrointestinal tract include tablets, capsules, oral solutions, oral emulsions, suppositories and granules; and the preparations administrated by injection include injection solutions, injection emulsions, injection sustained-release solutions, and injection suspensions;

in a fifth aspect, a use of the above pharmaceutical composition or preparation containing the main group metal complex having the structure represented by Formula I or Formula II, or pharmaceutically acceptable salt, solvate, non-covalent bond compound or prodrug thereof in preparing drugs against cancers, including breast cancer, liver cancer, lung cancer, melanoma, prostate cancer, colon cancer, colorectal cancer, glioblastoma, kidney cancer, pancreatic cancer, gastric cancer, lymphoma, cervical cancer, ovarian cancer, esophageal cancer, nasal cancer, leukemia, breast duct cancer, gallbladder cancer, testicular cancer, cardia cancer and thyroid cancer, wherein the drugs are administered at a dosage of 0.01 to 200 mg/kg body weight per day or 0.5 to 14 g to each patient per day;

in a sixth aspect, a use of the main group metal complex having the structure represented by Formula I or Formula II, or pharmaceutically acceptable salt, solvate, non-covalent bond compound or prodrug thereof in optical labeling, especially fluorescent labeling, and preferably in fluorescence imaging, targeted preparations, administration monitoring, luminescent materials, organic light-emitting diodes, and dye-sensitized solar cells.

Particularly, the present invention provides a main group metal complex, which is composed of a planar tetradentate Schiff base ligand, a p-block main group metal ion and an axial monodentate ligand, and has the structure as shown below:

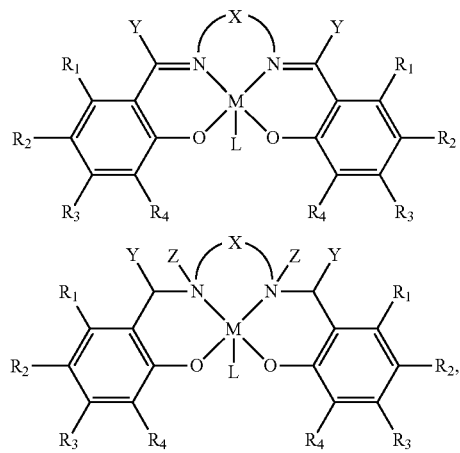

wherein M represents the p-block main group metal; X represents the diamine residue, and nitrogen atoms on each side of X are connected by $C_{1-5}$ aliphatic chain or substituted aliphatic chain, or exist as ortho substituents of an aromatic ring; Y is hydrogen or alkyl; $R_1$, $R_2$, $R_3$ and $R_4$ are each independently selected from hydrogen, halogen, nitro, hydroxyl, amino, substituted amino, alkyl, alkoxy, halogen substituted alkyl, mercapto or alkylthio, and the two adjacent substituents, i.e. $R_1$ and $R_2$, $R_2$ and $R_3$ and/or $R_3$ and $R_4$ can form a ring; L represents one or more axial monodentate ligands of halogen, oxygen coordinating small molecule or nitrogen coordinating small molecule; Z is hydrogen or alkyl.

M preferably is aluminum, gallium, indium, thallium, germanium, tin, or lead.

X represents benzene, substituted benzene or pyridine ring, or a $C_1$-$C_3$ aliphatic chain or substituted aliphatic chain.

The halogen is selected from one or more of F, Cl, Br and I; the alkyl group is a $C_1$-$C_{12}$ alkyl; the substituted amino group is a $C_1$-$C_{12}$ alkyl-substituted amino group; the alkoxy group is $C_1$-$C_8$ alkoxy; the halogen-substituted alkyl group is a $C_1$-$C_{12}$ alkyl group substituted by one or more halogens; the alkylthio group is a $C_1$-$C_8$ alkyl-substituted mercapto group; the oxygen coordinating small molecule is selected from one or more of methanol, ethanol, acetone, dimethyl sulfoxide, tetrahydrofuran and water; the nitrogen coordinating small molecule is selected from one or more of pyridine, piperidine, n-propylamine, ethylenediamine and ethanolamine.

$R_1$ and $R_2$, $R_2$ and $R_3$ and/or R; and $R_4$ form a ring, and represent 1,3-butadiene-1,4-diyl or 1,4-dibutyl together.

The main group metal complex according to the present invention is one of those as follows:

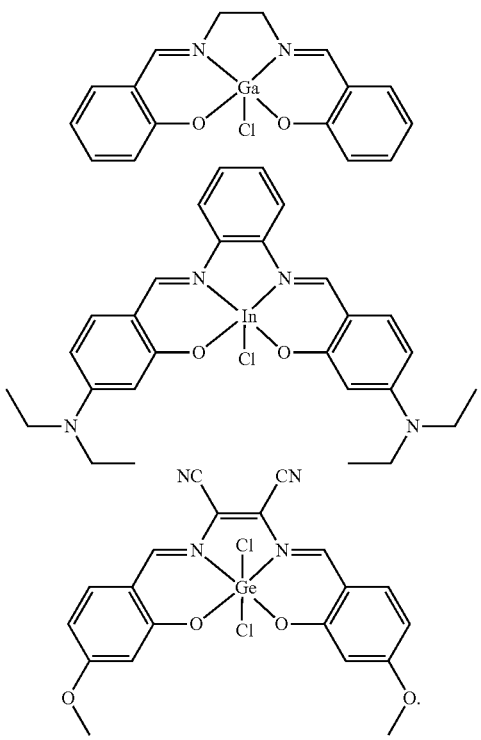

The main group metal complex according to the present invention is prepared following the reaction scheme below:

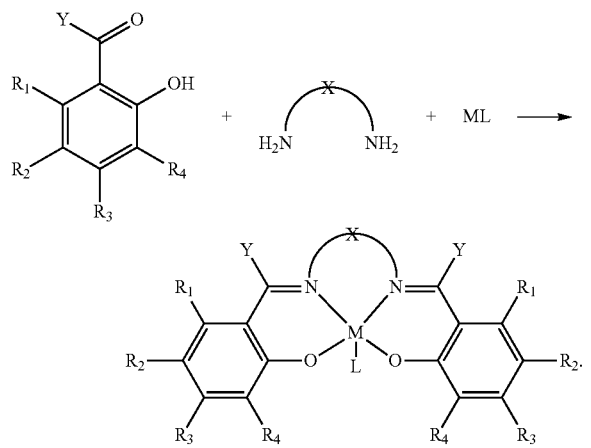

As shown in the above reaction scheme, the salicylaldehyde or substituted salicylaldehyde, the diamine precursor, and the main group metal salt MD are added in the organic solvent L, and the reaction is carried out at a temperature of 50 to 150° C. for 12 to 24 h, and then the complex represented by formula I can be obtained in one step. X, Y, M, L, $R_1$, $R_2$, $R_3$ and Ra are same as those described above.

Alternatively, the main group metal complex according to the present invention is prepared following the reaction scheme below:

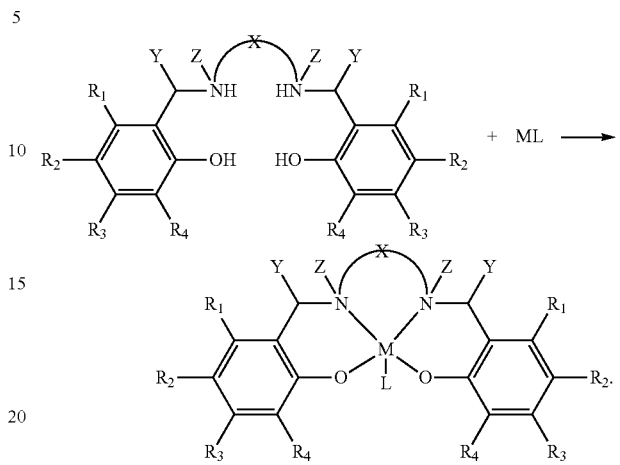

As shown in the above reaction scheme, the complex and the main group metal salt MD are added in the organic solvent L, and the reaction is carried out at a temperature of 50 to 150° C. for 12 to 24 h, and then the complex represented by formula II can be obtained in one step. X, Y, Z, M, L, $R_1$, $R_2$, $R_3$ and $R_4$ are same as those described above.

The organic solvent used in the above two reactions can be methanol, ethanol or acetonitrile. After the reaction, recrystallization will be carried out with acetonitrile/ether based solvent to make the complex solid precipitate out of the system.

The main group metal complex according to the present invention can be used to prepare the anticancer drugs.

The main group metal complex, and its preparation method and use provided according to the present invention have the following beneficial effects, i.e.
1) the main group metal complex according to the present invention shows high cytotoxicity to a variety of cancer cell lines, has selective killing effect, and is more effective than the conventional metal anticancer drugs;
2) the main group metal complex according to the present invention has excellent fluorescence properties and can be used as an optical label for fluorescent labeling, especially single- or double-photon(s) fluorescent labeling, such as in vivo imaging tracking, targeted preparations, administration monitoring, and luminescent materials;
3) the main group metal complex according to the present invention can be easily obtained by the simple preparation method thereof.

DESCRIPTION OF THE PREFERRED EMBODIMENTS

Figure 1:
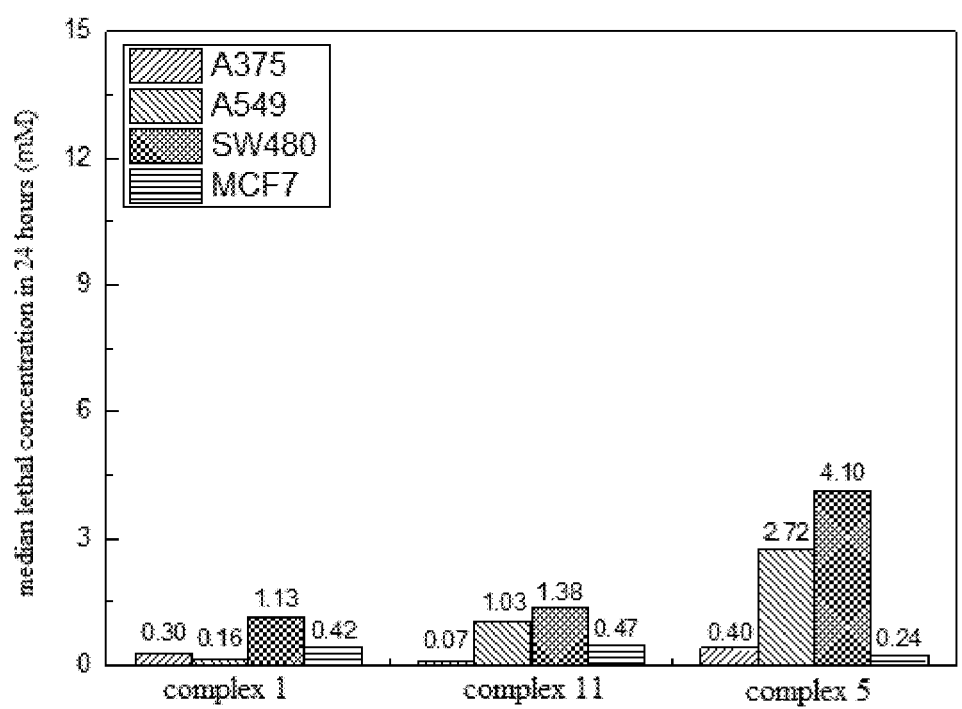
FIG. 1 shows the median lethal concentrations of the complex against different cancer cell lines according to Experiment 1.

Hereafter, the present invention will be described in detail, and the features and the advantages of the invention thus will become much clearer and obvious with the following exemplary description.

The term "exemplary" herein means "taking an example, an embodiment, or an illustration." Any embodiment described exemplarily herein should not be considered as being superior or better than other embodiments.

The present invention provides a main group metal complex having the structure represented by Formula I or Formula II as below, or pharmaceutically acceptable salt, solvate, non-covalent bond compound or prodrug thereof,

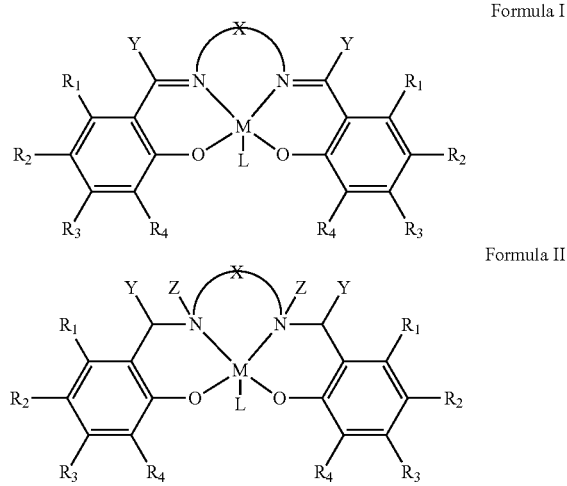

Formula I

Formula II which, including its cation, is composed of planar tetradentate Schiff base ligands and p-block main group metal ions, wherein, M represents the p-block main group metal;

X represents a diamine residue, and nitrogen atoms on each side of its imine bond are connected by substituted or unsubstituted $C_{1-12}$ alkyl or $C_{2-12}$ alkenyl, or X exists as ortho-substituents of a substituted or unsubstituted aryl or heterocyclic aryl;

Y is hydrogen, $C_{1-12}$ alkyl, halogen, halogen-substituted alkyl, cyano, amino, carbonyl, $C_{1-12}$ alkoxy or substituted amino;

Z is hydrogen, $C_{1-12}$ alkyl, halogen, nitro, hydroxyl, mercapto or carboxyl;

$R_1$, $R_2$, $R_3$ and Ra are substituents on the benzene ring of the corresponding ligand, and are each independently selected from hydrogen, halogen, nitro, hydroxyl, mercapto, carboxyl, amino, cyano, $C_{1-12}$ alkyl, $C_{2-12}$ alkenyl, $C_{2-12}$ alkynyl, $C_{1-8}$ alkoxy, $C_{2-8}$ alkenyloxy, $C_{2-8}$ alkynyloxy, $C_{1-8}$ alkylthio, $C_{3-8}$ heterocyclyl, aryl, $C_{1-8}$ alkanoyl, $C_{1-8}$ alkamido, $C_{1-8}$ alkylsulfonyl, arylsulfonyl, $C_{1-12}$ alkyl substituted amino or halogen substituted $C_1$-12 alkyl, or two adjacent substituents among $R_1$, $R_2$, $R_3$ and $R_4$ ($R_1$ and $R_2$, $R_2$ and $R_3$ and/or R; and $R_4$) may form a ring.

In this invention, the p-block main group metals refer to metal elements among the p-block main group elements defined according to the current periodic table, and generally refer to the metals of group 13, i.e. aluminum, gallium, indium, thallium and the metals of group 14, i.e. germanium, tin, lead.

M in Formula I or Formula II is one of aluminum, gallium, indium, thallium, germanium or tin, preferably is one of aluminum, gallium, indium, thallium or germanium, and most preferably is one of aluminum, gallium, indium or germanium.

In this invention, unless otherwise stated, the carbon atoms of the alkyl, alkenyl, alkynyl, alkoxy, alkenyloxy, alkynyloxy, alkylthio, heterocyclyl, aryl, heterocyclic aryl, alkanoyl, alkamido, alkylsulfonyl, arylsulfonyl, alkylamino and hydrocarbyl substituted amino can be substituted or not substituted by halogen, nitro, hydroxyl, mercapto, carboxyl, amino, cyano or carbonyl.

The term "alkyl" herein refers to a linear, branched or cyclic saturated hydrocarbon group, for example, methyl, ethyl, propyl, isopropyl, butyl, tert-butyl, cyclohexyl and 2-ethyl-4 propyl-cyclohexyl. $C_{1-12}$ refers to a hydrocarbon chain with 1-12 carbon atoms.

The term "alkenyl" herein refers to a hydrocarbon group containing an alkenyl group in a linear, branched or cyclic hydrocarbon chain, and the carbon atom on the alkenyl can be connected or not connected to the carbon atom on the phenyl of the ligand, for example, vinyl, 1-allyl, 1-phenylallyl, and 2-methpropenyl. Similarly, $C_{2-12}$ alkenyl refers to the alkenyl group with 2-12 carbon atoms.

The term "alkynyl" herein refers to a linear, branched or cyclic hydrocarbon group including an alkynyl group, and the carbon atom on the alkynyl can be connected or not connected to the carbon atom on the phenyl of the ligand, for example, propynyl, propargyl, 2-methylbutynyl. Similarly, $C_{2-12}$ alkynyl refers to the alkynyl group with 2-12 carbon atoms.

The term "alkoxy" herein refers to the alkyl including an oxyether group, such as methoxy group, ethoxy group, and propoxy group. $C_{1-8}$ alkoxy refers to the alkoxy group with 1-8 carbon atoms.

The term "alkenyloxy" herein refers to a linear, branched or cyclic hydrocarbon group with an alkenyl group including an oxyether group. $C_{2-8}$ alkenyloxy refers to the alkenyloxy group with 2-8 carbon atoms.

The term "alkynyloxy" herein refers to a linear, branched or cyclic hydrocarbon group with an alkynyl group including an oxyether group. $C_{2-8}$ alkynyloxy refers to the alkynyloxy group with 2-8 carbon atoms.

The term "alkylthio" herein refers to the alkyl including a thioether group, such as methylthio, ethylthio, and propylthio. $C_{1-8}$ alkylthio refers to the alkylthio group with 1-8 carbon atoms.

The term "heterocyclyl" herein refers to a stable 3-8 membered saturated cyclic group containing one or more heteroatom(s), which can be connected or not connected to the benzene of the ligand, preferably connected. Typical heteroatoms include oxygen, sulfur and nitrogen. For example, it can be tetrahydropyrrolyl, quinoline, thiophene, furan and the like. $C_{3-8}$ heterocyclic group refers to the heterocyclic group with 3-8 carbon atoms.

The term "aryl" herein refers to an aromatic ring containing a phenyl group, generally is benzene, naphthalene, anthracene or phenanthrene, and preferably is benzene and naphthalene.

The term "heterocyclic aryl" herein refers to a monoaromatic ring or polyaromatic ring group including one or more heteroatom(s), preferably a 5-10 membered ring. The polyaromatic ring group may be a double monoaromatic ring, a benzo monoaromatic ring or a condensed aromatic ring group. For example, the aryl group may be furan, pyridine, thiophene, imidazole, pyrrole, pyridazine, pyrazine, benzopyrrole, benzofuran, benzisoquinoline, pyrazinopyridazine, or the like.

The term "alkanoyl" herein refers to the alkyl including an acyl group. $C_{1-8}$ alkanoyl group refers to the alkanoyl group with 1-8 carbon atoms.

The term "alkamide" herein refers to the alkyl including an alkamide group. $C_{1-8}$ alkamide group refers to the alkamide group with 1-8 carbon atoms.

The term "alkylsulfonyl" herein refers to the alkyl including an alkylsulfonyl group. $C_{1-8}$ alkylsulfonyl group refers to the alkylsulfonyl group with 1-8 carbon atoms.

The term "arylsulfonyl" herein refers to the aryl including a sulfonyl group.

The term "alkyl-substituted amino" herein refers to an amino group substituted by the alkyl group, such as methylamino, ethylamino, dimethylamino, and diethylamino. $C_{1-12}$ alkylamino group refers to the alkylamino group with 1-12 carbon atoms in the alkyl substituent.

Further, the nitrogen atoms on each side of X are connected by an aliphatic chain or a substituted aliphatic chain with a carbon number of 1 to 5, or exist as ortho substituents of the aromatic ring.

Preferably, X in Formula I or Formula II is selected from —CH$_2$—, —CH$_2$—CH$_2$—, —CH(CH$_3$)—CH$_2$—, —CH(CN)—CH(CN)—, —CH(CN)—CH$_2$—, —CH$_2$(Cl)—CH(CN)—, —CH$_2$(OH)—CH(CN)—, —CH$_2$(Cl)—CH$_2$—, —CH$_2$(OH)—CH$_2$—, —CH═CH—, —CO—CH(CN)—, —C(CN)═C(CN)—, —CH═C(CN)—, —CH═C(Cl)—, —CH═CH—CH═CH—, —CH═C(CN)—CH═CH—, —CH═C(NH$_3$)— or —CO—CH$_2$—, or acts as an ortho-disubstituted group of the substituted or unsubstituted benzene, naphthalene, anthracene, phenanthrene, pyridine, imidazole, pyrrole, thiophene, furan, benzopyrrole or benzofuran. When X is a cyclic group, it is connected to the imino group of the corresponding ligand through two adjacent cyclic backbone atoms.

More preferably, X is selected from —CH$_2$—, —CH$_2$—CH$_2$—, —CH(CN)—CH(CN)—, —CH(CN)—CH$_2$—, —CH$_2$(Cl)—CH(CN)—, —CH$_2$(Cl)—CH$_2$—, —CH$_2$(OH)—CH$_2$—, —CH═CH—, —C(CN)═C(CN)—, —CH═C(CN)—, —CH═C(Cl)— or —CH═C(NH$_3$)—, or acts as an ortho-disubstituted group of benzene, pyridine, benzopyridine, imidazole, furan, cyano-substituted benzene, naphthalene, cyano-substituted naphthalene.

In some preferred embodiments, X in Formula I and the two imino groups in the corresponding ligand may form a conjugated structure.

In these embodiments, X may be selected from ethylene, cyano-substituted ethylene, 1,3-butadiene, cyano-substituted 1,3-butadiene, benzene, pyridine, benzopyridine, naphthalene, cyano-substituted naphthalene.

Preferably, X in Formula I or Formula II is selected from ethylene, cyano-substituted ethylene, 1,3-butadiene, benzene, cyano-substituted benzene, pyridine or cyano-substituted pyridine.

Most preferably, X is selected from —CH═CH—, —C(CN)═C(CN)—, —CH═C(CN)—, —CH═C(CN)—CH═CH—, —CH═C(NH$_3$)— or —CO—CH$_2$—, or acts as an ortho-disubstituted group of those as follows:

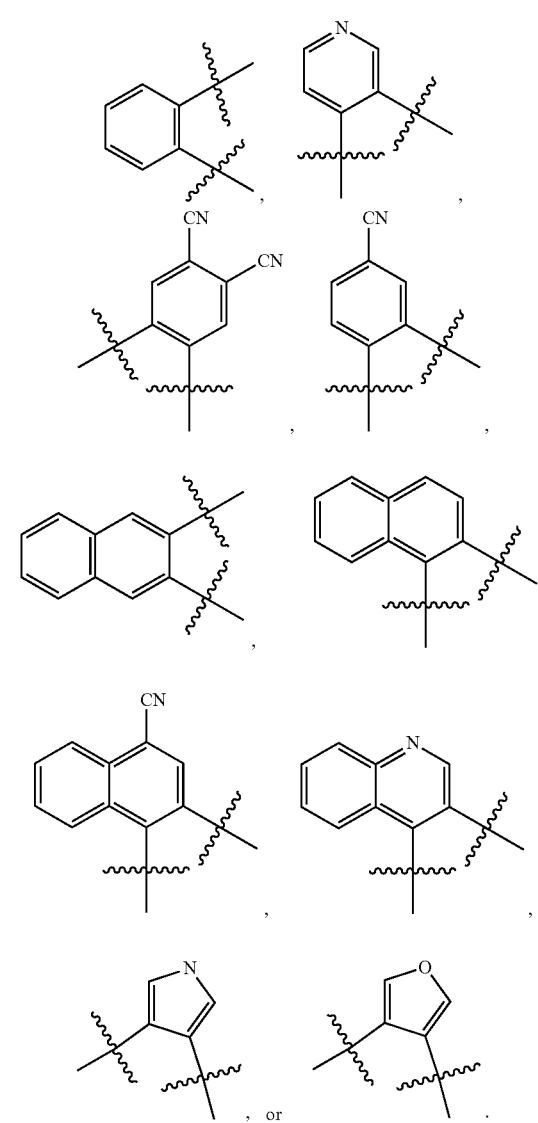

, or .

In some preferred embodiments, X is —C(CN)═C(CN)—.

In some preferred embodiments, X is phenyl group.

In some preferred embodiments, X is 4-cyano substituted phenyl group.

In some preferred embodiments, X is 4,5-dicyano substituted phenyl group.

In some preferred embodiments, X is

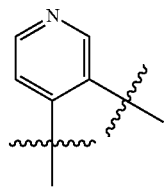

In some embodiments, X in Formula I or Formula II is a substituted or unsubstituted saturated alkyl group. In these embodiments, X is preferably selected from —CH$_2$—, —CH$_2$—CH$_2$—, —CH$_2$(Cl)—CH$_2$—, —CH(CN)—CH(CN)—, —CH$_2$(OH)—CH$_2$— or —CH$_2$(CH$_3$)—CH$_2$—, and more preferably is —CH$_2$—, —CH$_2$—CH$_2$—, —CH$_2$(Cl)—CH$_2$— or —CH$_2$(CH$_3$)—CH$_2$—.

Further, Y in Formula I or Formula II is hydrogen, halogen, cyano, C$_{1-4}$ alkyl or C$_{1-4}$ alkoxy, wherein halogen includes F, Cl, Br and I.

When Y in Formula I or Formula II is an alkyl group, it is more preferably a C$_{1-3}$ alkyl.

Preferably, Y is hydrogen, halogen, cyano, methyl, ethyl, isopropyl, methoxy, ethoxy, halogen-substituted C$_1$-3 alkyl or halogen-substituted C$_1$-3 alkoxy.

More preferably, Y is hydrogen, halogen, cyano, methyl or methoxy.

Z is hydrogen, C$_{1-10}$ alkyl, halogen, nitro, hydroxyl, mercapto or carboxyl. Preferably, Z is hydrogen, C$_{1-6}$ alkyl, halogen, nitro, hydroxyl, mercapto or carboxyl.

In some embodiments, Z is hydrogen.

In the main group metal complex according to the present invention, R$_1$, R$_2$, R$_3$ and R$_4$ are each independently selected from hydrogen, halogen, nitro, hydroxyl, mercapto, carboxyl, amino, cyano, C$_{1-12}$ alkyl, C$_{2-12}$ alkynyl, C$_{2-12}$ alkynyl, C$_{1-8}$ alkoxy, C$_{2-8}$ alkenyloxy, C$_{2-8}$ alkynyloxy, C$_{1-8}$ alkylthio, C$_{3-8}$ heterocyclyl, aryl, C$_{1-8}$ alkanoyl, C$_{1-8}$ alkamido, C$_{1-8}$ alkylsulfonyl, arylsulfonyl, N, N-bis(C$_{1-6}$ alkyl)amino, N—(C$_{1-6}$ alkyl)-N—(C$_{1-6}$ alkyl)amino, N—(C$_{1-6}$ alkyl)-N—(C$_{1-6}$ alkynyl)amino, N,N-diarylamino, N—(C$_{1-6}$ alkyl)-N-arylamino, N—(C$_{1-6}$ alkyl)-N-heterocyclylamino, —CF$_3$—, —ClCH$_2$—, —ClCH$_2$—CH$_2$—, (CH$_3$)$_2$C(CH$_2$Cl)—, CH$_2$—CH$_2$Cl—CH(CH$_3$)$_2$— or halogen-substituted C$_{36}$ cyclic alkyl group. C$_{36}$ cyclic alkyl group includes halogen-substituted cyclohexyl, halogen-substituted cyclopentyl, and halogen-substituted methylcyclopentyl.

Preferably, R$_1$, R$_2$, R$_3$ and R$_4$ in Formula I or Formula II are each independently selected from hydrogen, fluorine, chlorine, bromine, iodine, nitro, hydroxyl, mercapto, amino, cyano, C$_{1-5}$ alkyl, C$_{14}$ alkylthio, C$_{1-4}$ alkoxy, C$_{1-8}$ alkylamino, N,N-bis(C$_{1-6}$ alkyl)amino, N—(C$_{1-6}$ alkyl)-N—(C$_{1-6}$ alkyl)amino, N—(C$_{1-6}$ alkyl)-N—(C$_{36}$ alkynyl)amino, C$_{3-8}$ unsaturated heterocyclic group, C$_{3-8}$ saturated heterocyclic group, halogen substituted C$_{5-6}$ cyclic alkyl or halogen-substituted C$_{1-6}$ alkyl.

In some preferred embodiments, R$_1$, R$_2$, and Ra in Formula I or Formula II are each independently selected from hydrogen, cyano, mercapto, C$_{2-4}$ alkylthio or C$_{1-5}$ alkyl.

In some preferred embodiments, in Formula I or Formula II, R$_1$ is hydrogen, R$_4$ is hydrogen, cyano or C$_{1-5}$ alkyl, and R$_2$ is hydrogen, mercapto, C$_{2-4}$ alkylthio or C$_{1-5}$ alkyl.

In some preferred embodiments, in Formula I or Formula II, R$_1$ and R$_2$ are hydrogen, and R$_4$ is mercapto or C$_{2-4}$ alkylthio.

In some preferred embodiments, in Formula I or Formula II, R$_1$ and Ra are hydrogen, and R$_2$ is mercapto or C$_{2-4}$ alkylthio.

In some preferred embodiments, in Formula I or Formula II, R$_1$, R$_2$ and R$_4$ are hydrogen.

R$_3$ in Formula I or Formula II is selected from hydrogen, fluorine, chlorine, amino, C$_{1-8}$ alkylamino, C$_{1-4}$ alkoxy, N,N-bis(C$_{1-5}$ alkyl)amino, N—(C$_{1-6}$ alkyl)-N—(C$_{1-4}$ alkyl) amino, N—(C$_{1-4}$ alkyl)-N—(C$_{3-5}$ alkynyl)amino, C$_{3-8}$ unsaturated nitrogen heterocyclyl or C$_{3-8}$ saturated nitrogen heterocyclyl.

Preferably, R$_3$ in Formula I or Formula II is selected from hydrogen, C$_{1-4}$ alkoxy, N, N-bis(C$_{1-5}$ alkyl)amino, N—(C$_{1-4}$ alkyl)-N—(C$_{1-2}$ alkyl)amino, N—(C$_{1-4}$ alkyl)-N—(C$_{3-5}$ alkynyl)amino, or C$_{3-5}$ saturated nitrogen heterocyclyl.

More preferably, R$_3$ in Formula I or Formula II is selected from hydrogen, methoxy, ethoxy, isopropoxy, N,N-dimethylamino, N,N-diethylamino, N,N-dipropylamino, N-(2-methyl butyl) amino, N-butyl-N-methylamino, N-ethyl-N-methylamino, N-butyl-N-ethylamino, N-propargyl-N-methyl amino, N-alkynylbutyl-N-ethylamino, tetrahydropyrrole, hydrogenated pyridine or hydrogenated imidazole.

In some preferred embodiments, R$_3$ in Formula I or Formula II is N,N-dimethylamino, and R$_4$ is C$_{2-4}$ alkylthio.

In some preferred embodiments, R$_3$ in Formula I or Formula II is N,N-diethylamino, and R$_4$ is mercapto, C$_{1-4}$ alkyl or C$_{1-4}$ alkoxy.

In some preferred embodiments, R$_3$ in Formula I or Formula II is hydrogen, methoxy, N,N-diethylamino, N,N-dimethylamino, N-methyl-N-n-butylamino, N-methyl-N-propargylamino or tetrahydropyrrole, and R$_4$ is hydrogen.

In some preferred embodiments, R$_1$, R$_2$, R$_3$ and R$_4$ in Formula I or Formula II are hydrogen.

In the main group metal complex according to the present invention, two adjacent substituents among R$_1$, R$_2$, R$_3$ and R$_4$ (R$_1$ and R$_2$, R$_2$ and R; and/or R$_3$ and R$_4$) may also form a ring.

When R$_1$ and R$_2$, R$_2$ and R$_3$ and/or R$_4$ and R$_4$ form a ring, they represent, for example, 1,3-butadiene-1,4-diyl or 1,4-dibutyl, etc., and are combined with the benzene ring to form naphthalene or tetrahydronaphthalene, etc.

In some embodiments, in Formula I or Formula II, R$_2$ and R$_3$ or R$_3$ and R$_4$ preferably form a ring as follows:

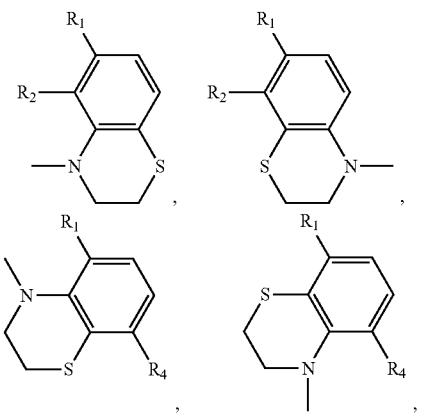

-continued

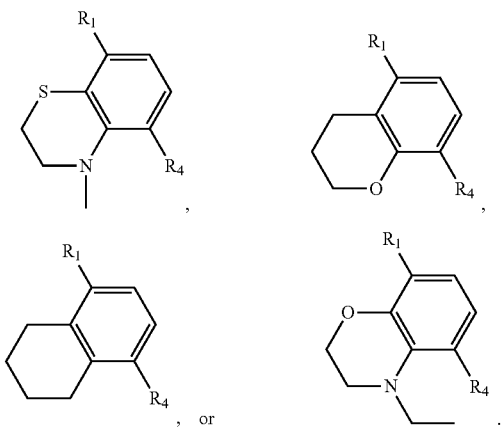

In some embodiments, in Formula I or Formula II, both $R_2$ and $R_3$, and, $R_3$ and $R_4$ form rings, preferably as follows:

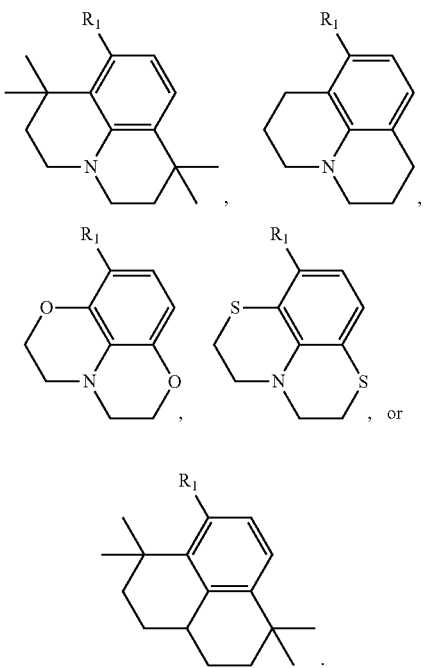

Preferably, the main group metal complex having the structure represented by Formula I or Formula II further has ligands represented by Formula III and Formula IV as below:

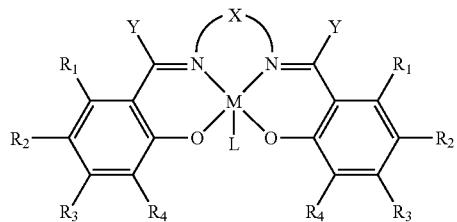

Formula III

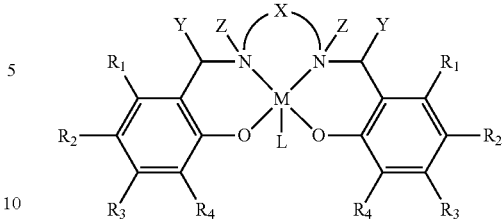

Formula IV

Wherein L represents one or more axial monodentate ligands, including anionic ligands and neutral ligands. L may also be a non-coordinating anion. Preferably, the anionic ligand includes halogen ions such as fluorine, chlorine, bromine, iodide ions, and acetate ions. The neutral ligand is an oxygen coordinating or nitrogen coordinating ligand, preferably derived from a solvent molecule.

The oxygen coordinating solvent molecule is one or more selected from methanol, ethanol, acetone, dimethyl sulfoxide, tetrahydrofuran, water, isopropanol, glycerin, formaldehyde, acetic acid, formic acid, ether and dimethyl sulfoxide. The nitrogen coordinating solvent molecule is one or more selected from pyridine, piperidine, n-propylamine, ethylenediamine, ethanolamine, dimethylformamide, acetonitrile, ammonia and triethylamine.

Preferably, L is selected from fluoride, chloride, bromide, acetate, methanol, ethanol, isopropanol, acetone, dimethylsulfoxide, dimethylformamide, pyridine or acetonitrile.

Further, the present invention provides a main group metal complex, which is composed of a planar tetradentate Schiff base ligand, a p-block main group metal ion and an axial monodentate ligand. In Formula III and Formula IV, M represents the p-block main group metal; X represents the diamine residue, and nitrogen atoms on each side of X are connected by $C_{1-5}$ aliphatic chain or substituted aliphatic chain, or X exists as ortho substituents of an aromatic ring such as benzene, substituted benzene, pyridine; Y is hydrogen or alkyl; $R_1$, $R_2$, $R_3$ and $R_4$ are substituents on benzene of the corresponding ligand backbone, and each independently selected from hydrogen, halogen, nitro, hydroxyl, amino, substituted amino, alkyl, alkoxy, halogen substituted alkyl, mercapto or alkylthio, and two adjacent substituents, i.e. $R_1$ and $R_2$, $R_2$ and $R_3$ and/or Ra and Ra can form a ring; L represents one or more axial monodentate ligands of halogen, oxygen coordinating small molecule or nitrogen coordinating small molecule; and Z in Formula II is hydrogen or alkyl.

Preparably, M is one of group 13 metals (aluminum, gallium, indium, thallium) or group 14 metals (germanium, tin, lead).

X is an aromatic ring such as benzene, substituted benzene and pyridine, or a $C_1$-$C_3$ aliphatic chain or substituted aliphatic chain, wherein the substituent of the aliphatic chain is, for example, cyano. In some embodiments, X is —$CH_2$—$CH_2$—, ortho-disubstituted benzene, —C(CN)—C(CN)—, or the like.

Halogen includes F, Cl, Br and I.

The alkyl group is preferably $C_1$-$C_{12}$ alkyl, more preferably $C_1$-$C_6$ alkyl, such as methyl, ethyl, propyl, isopropyl, butyl.

The substituted amino group is preferably $C_1$-$C_{12}$ alkyl-substituted amino group, more preferably $C_1$-$C_6$ alkyl-substituted amino group, such as methylamino, ethylamino, dimethylamino, diethylamino.

The alkoxy group is preferably $C_1$-$C_8$ alkoxy, more preferably $C_1$-$C_4$ alkoxy, such as methoxy, ethoxy, propoxy.

The halogen-substituted alkyl group is preferably $C_1$-$C_{12}$ alkyl group substituted by one or more halogens, more preferably $C_1$-$C_6$ alkyl group substituted by one or more halogens, such as trifluoromethyl.

The alkylthio group is preferably $C_1$-$C_8$ alkyl-substituted mercapto group, more preferably $C_1$-$C_4$ alkyl-substituted mercapto group, such as methylthio, ethylthio, propylthio.

When $R_1$ and $R_2$, $R_2$ and $R_3$ and/or Ra and Ra form a ring, they represent 1,3-butadiene-1,4-diyl, 1,4-dibutyl, or the like, and are combined with the benzene ring to form naphthalene, tetrahydronaphthalene, or the like.

The oxygen coordinating solvent molecule is for example methanol, ethanol, acetone, dimethyl sulfoxide, tetrahydrofuran, water, or the like. The nitrogen coordinating solvent molecule is for example pyridine, piperidine, n-propylamine, ethylenediamine, ethanolamine, or the like.

The typical main group metal complexes includes for example those as below:

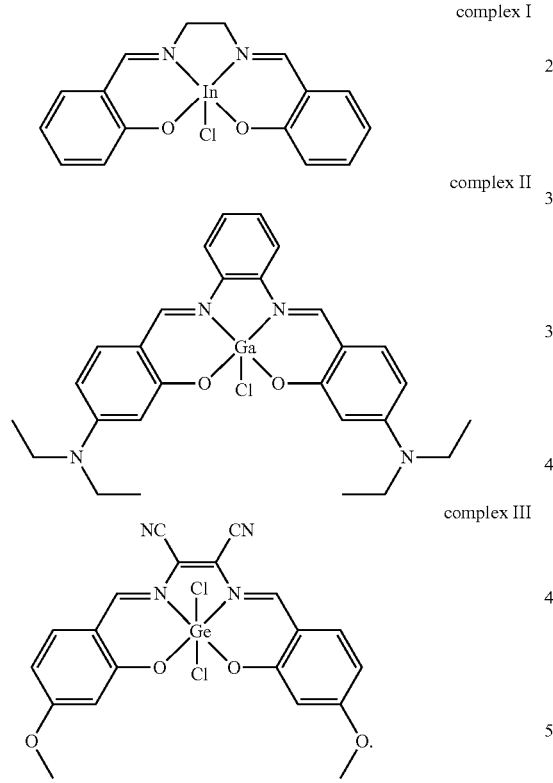

complex I complex II complex III

In the complex I, M is indium, L is chlorine, X is —$CH_2$—$CH_2$—, Y is hydrogen, and the salicylaldehyde residue has no modification on the benzene ring.

In the complex II, M is gallium, L is chlorine, X is ortho-disubstituted benzene, Y is hydrogen, and the modification on the benzene ring of the salicylaldehyde residue is a diethylamino at position $R_3$.

In the complex III, M is germanium, L is two chlorines, X is —C(CN)=C(CN)—, Y is hydrogen, and the modification on the benzene ring of the salicylaldehyde residue is a methoxy at position $R_3$.

Further, the present invention provides some examples of the main group metal complexes having the structure represented by Formula I or Formula II, including:

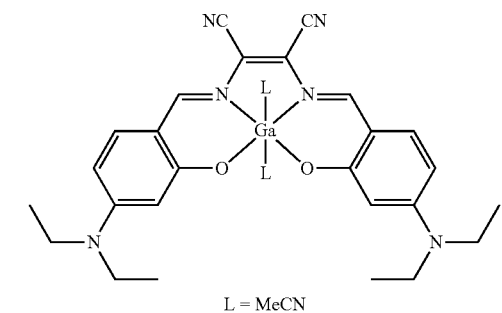

example 1

L = MeCN

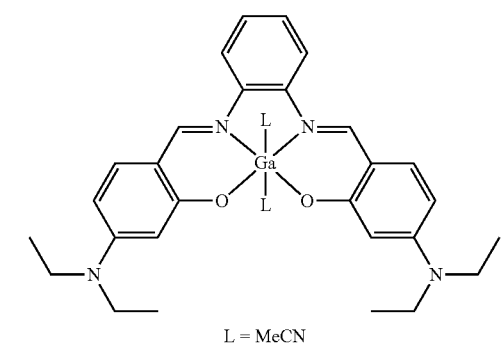

example 2

L = MeCN

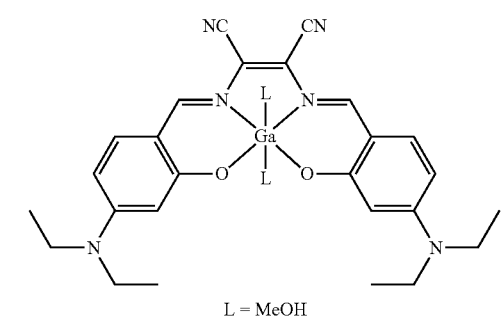

example 3

L = MeOH

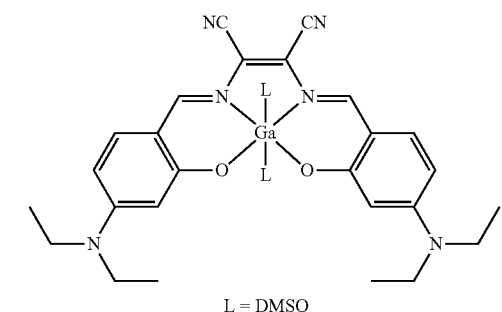

example 4

L = DMSO

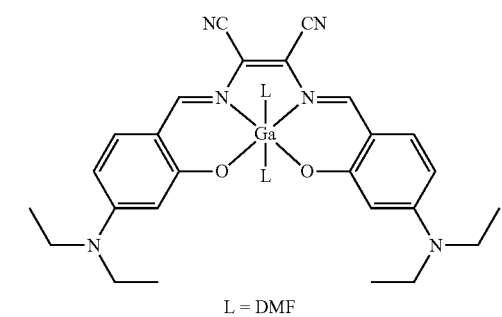

example 5

L = DMF

| | |
|---|---|
| 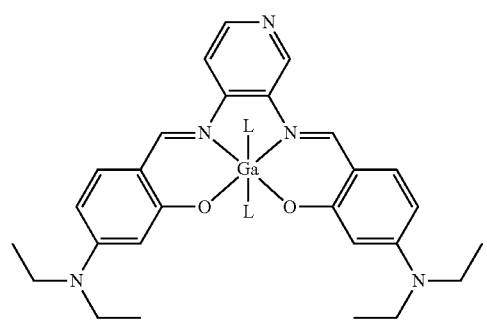 example 6 L = MeCN | 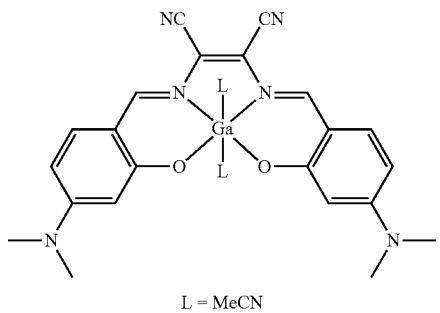 example 10 L = MeCN |
| 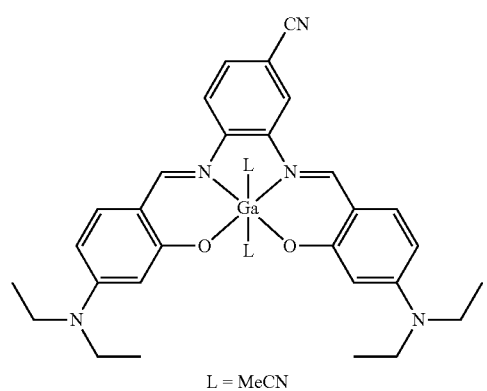 example 7 L = MeCN | 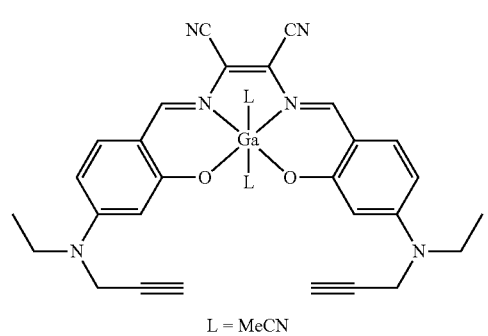 example 11 L = MeCN |
| 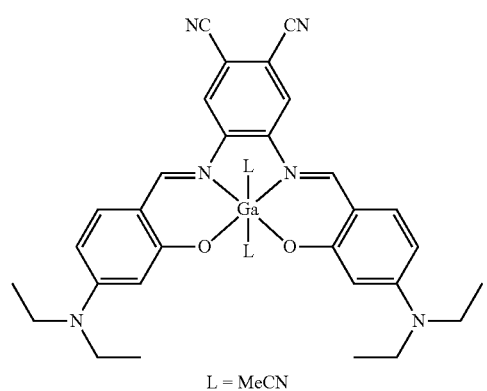 example 8 L = MeCN | 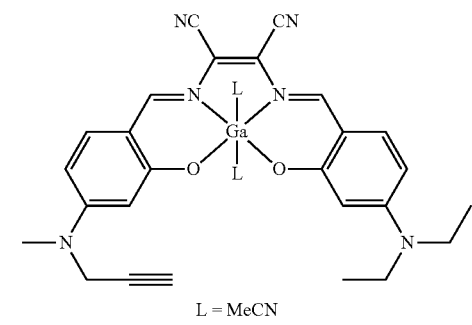 example 12 L = MeCN |
| 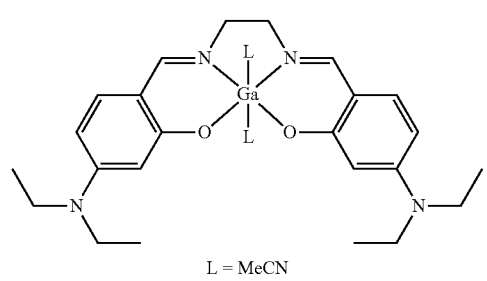 example 9 L = MeCN | 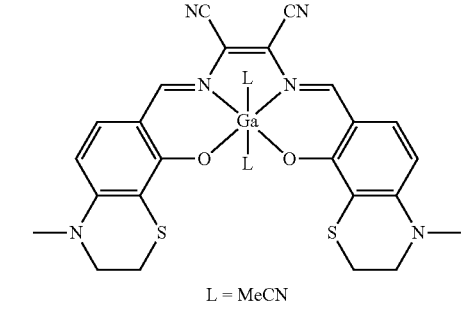 example 13 L = MeCN |
| | 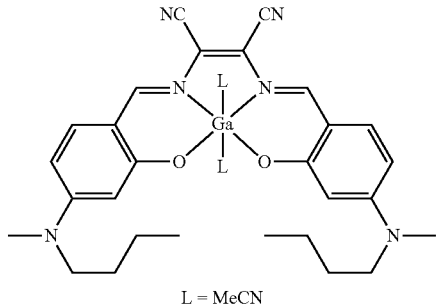 example 14 L = MeCN |

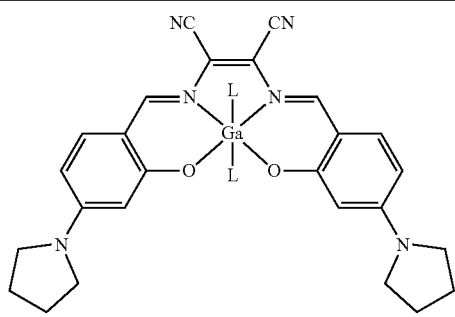
example 15
L = MeCN
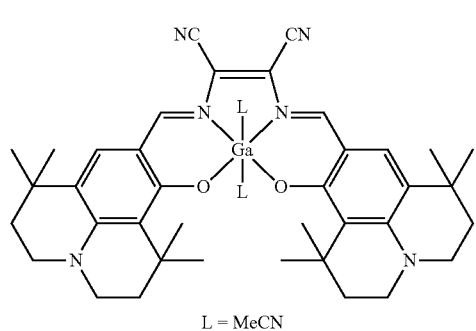
example 16
L = MeCN
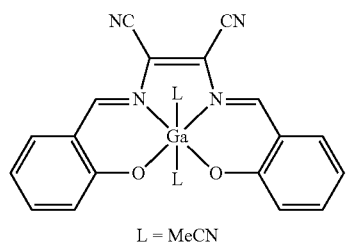
example 17
L = MeCN
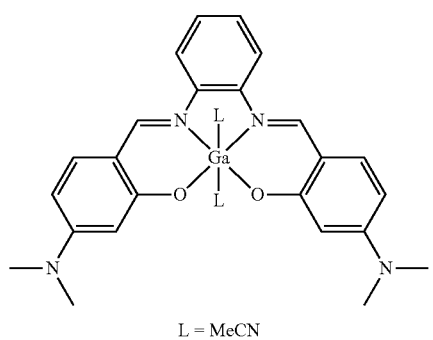
example 18
L = MeCN
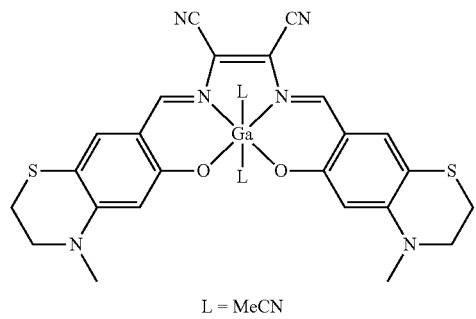
example 19
L = MeCN
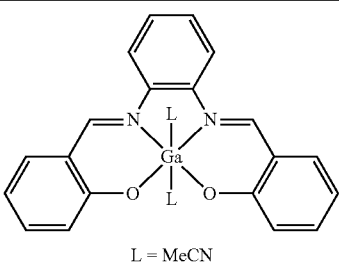
example 20
L = MeCN
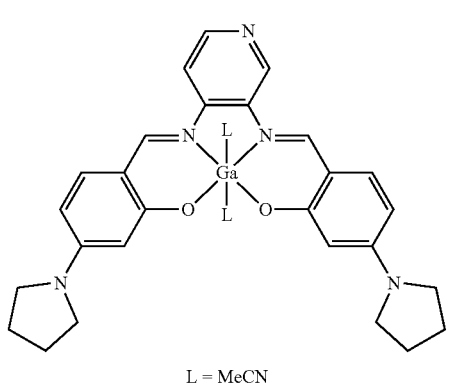
example 21
L = MeCN
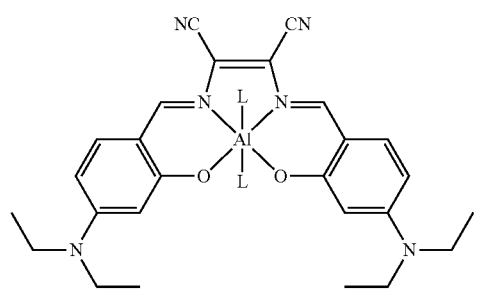
example 22
L = MeCN
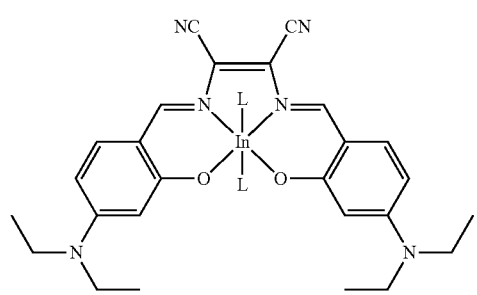
example 23
L = MeCN
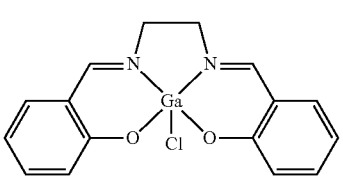
example 24

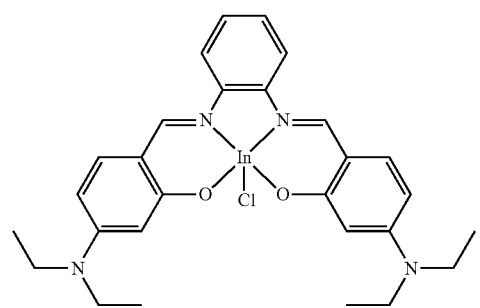
example 25
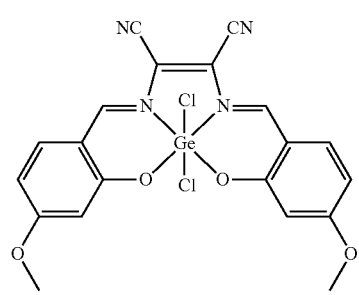
example 26
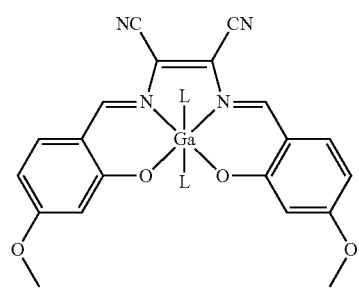
example 27
L = MeCN
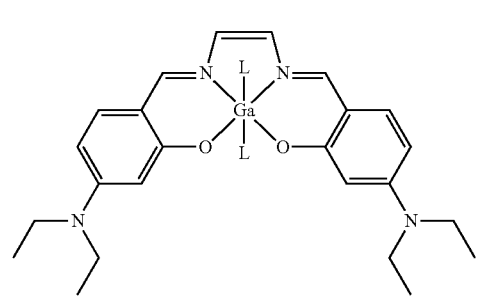
example 28
L = MeCN
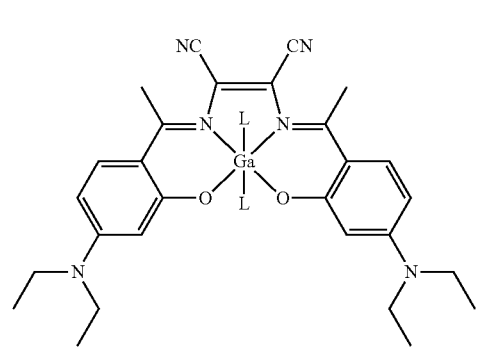
example 29
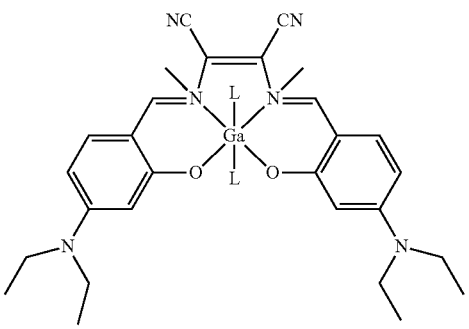
example 30
L = MeCN
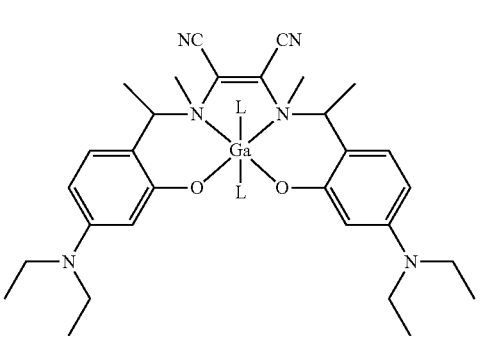
example 31
L = MeCN
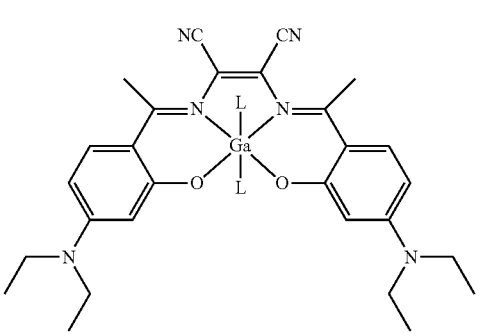
example 32
L = MeCN
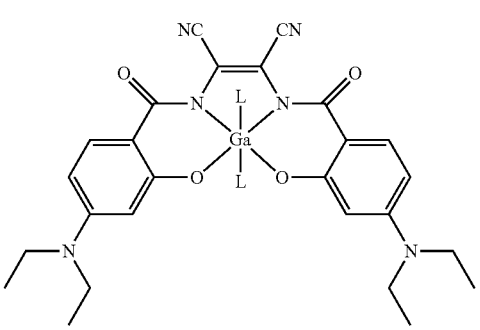
example 33
L = MeCN

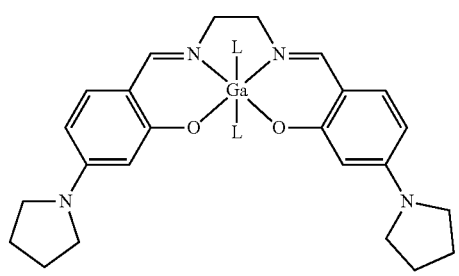

example 34

L = MeCN

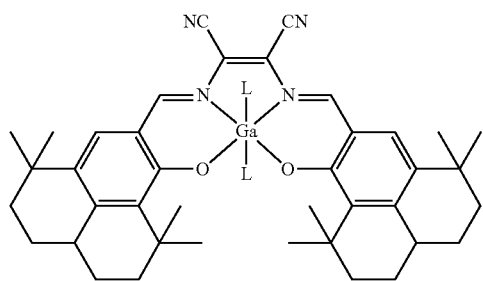

example 35

L = MeCN

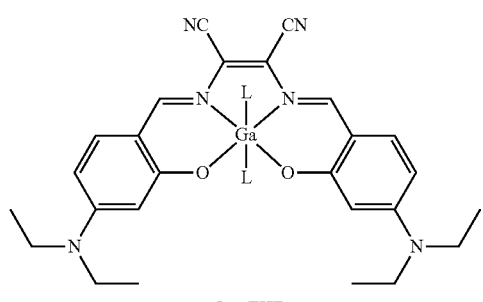

example 36

L = THF

The main group metal complex having the structure represented by Formula I or Formula II according to the present invention can also be present in the form of pharmaceutically acceptable salt, as shown in Formula V or Formula VI below:

Formula V

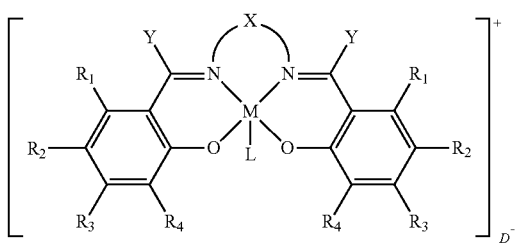

Formula VI

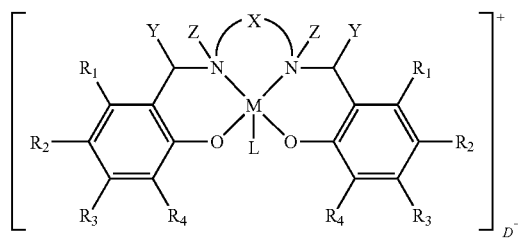

The salt of the compound according to the present invention refers to a non-toxic pharmaceutically acceptable salt, generally an inorganic acid salt or an organic acid salt. In Formula V or Formula VI, D-represents an acid radical of an inorganic acid or an organic acid forming a salt.

Typical organic or inorganic acids include hydrochloric acid, hydrobromic acid, hydroiodic acid, perchloric acid, nitric acid, acetic acid, sulfuric acid, propionic acid, glycolic acid, lactic acid, succinic acid, maleic acid, fumaric acid, malic acid, Tartaric acid, citric acid, benzoic acid, mandelic acid, methanesulfonic acid, benzenesulfonic acid, oxalic acid, p-toluenesulfonic acid, trifluoromethanesulfonic acid, cyclohexaminesulfonic acid, salicylic acid or trifluoroacetic acid.

Preferably, the inorganic acid or the organic acid is selected from hydrochloric acid, hydrobromic acid, perchloric acid, nitric acid, acetic acid, sulfuric acid, lactic acid, succinic acid, maleic acid, fumaric acid, malic acid, Tartaric acid, citric acid, benzoic acid, methanesulfonic acid, benzenesulfonic acid, oxalic acid, p-toluenesulfonic acid, trifluoromethanesulfonic acid, or salicylic acid.

More preferably, the inorganic acid or the organic acid is selected from hydrochloric acid, nitric acid, acetic acid, sulfuric acid, lactic acid, succinic acid, maleic acid, tartaric acid, methanesulfonic acid, benzenesulfonic acid, p-toluenesulfonic acid, trifluoromethanesulfonic acid or salicylic acid.

In some preferred embodiments, the pharmaceutically acceptable salt of the main group metal complex having the structure represented by Formula I or Formula II is hydrochloride, nitrate or triflate.

The main group metal complex having the structure represented by Formula I or Formula II according to the present invention can also be present in the form of a pharmaceutically acceptable solvate, non-covalent compound or prodrug.

The present invention further provides a method for preparing the main group metal complex having the structure represented by Formula I or Formula II, especially the structure represented by Formula III or Formula IV.

Wherein a salicylaldehyde or substituted salicylaldehyde represented by Formula V, a diamine precursor represented by Formula VI, and a main group metal salt MD are added in an organic solvent L, and the reaction is carried out at a temperature of 50 to 150° C. for 12 to 24 h, and then the target complex molecule is obtained in one step:

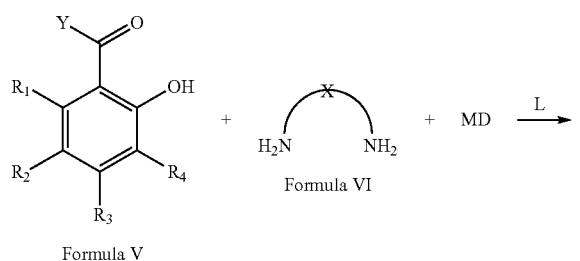

Formula V

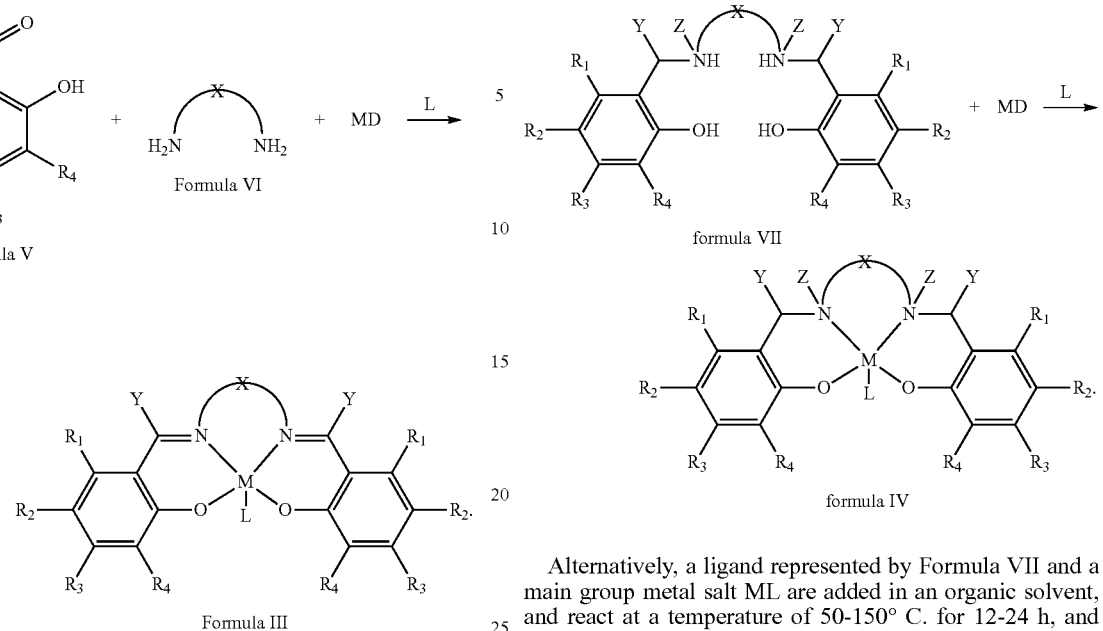

formula VII formula IV

Alternatively, a ligand represented by Formula VII and a main group metal salt ML are added in an organic solvent, and react at a temperature of 50-150° C. for 12-24 h, and then the target complex molecule is obtained in one step. The organic solvent can be methanol, ethanol, acetonitrile, or the like.

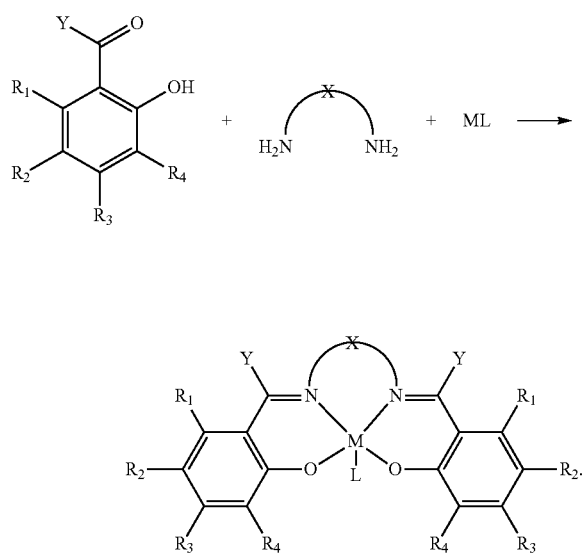

Formula III

Alternatively, asalicylaldehyde or substituted salicylaldehyde, a diamine precursor and a main group metal salt ML as shown below are added in an organic solvent, and react at a temperature of 50-150° C. for 12-24 h, and then the target complex molecule is obtained in one step. Most preferably, the reaction is carried out at 90° C. for 24 h. The organic solvent can be for example methanol, ethanol, acetonitrile, or the like. The reaction proceeds according to the following reaction scheme:

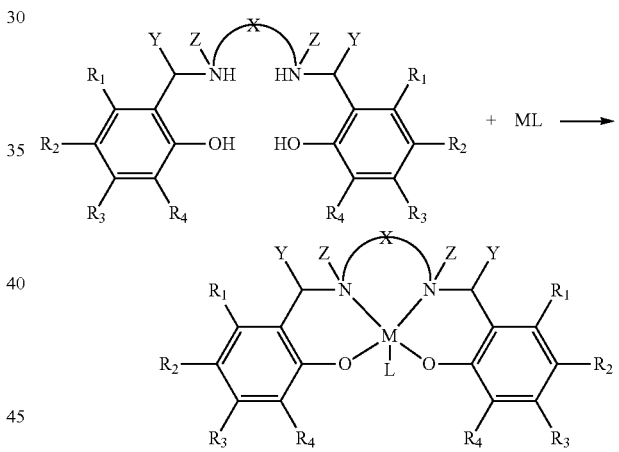

The complex represented by Formula IV can be obtained following the reaction scheme as below. Particularly, a ligand represented by Formula VII and a main group metal salt MD are added in an organic solvent L, and react at a temperature of 50-150° C. for 12-24 h, and then the target complex molecule is obtained in one step.

According to the present invention, MD represents a metal salt. Further, when M is $M^{2+}$, L is a neutral ligand, such as methanol, acetonitrile; when M is $M^{3+}$ or $M^{4+}$, L=D, which is an anionic ligand, such as chloride ion, bromide ion, acetate ion, or the like.

During the reaction, the organic solvent can be any selected from acetone, dimethylformamide, dimethylsulfoxide, pyridine, methanol, ethanol and acetonitrile. Preferably, the reaction is carried out at a temperature of 90-150° C. for 12-24 h.

The preparation method further comprises a post-treatment. Typically, the post-treatment is achieved by recrystallizating to make the product precipitate from the reaction system.

In a preferred embodiment, the post-treatment is carried out via recrystallization using the acetonitrile/ether solvent system, and consequently the complex solid can precipitate out of the system.

The main group metal complexes having the structure represented by Formula I or Formula II according to the present invention have significant toxicity and killing effect on various cancer cell lines. The median lethal concentration in 24 hours is generally below 2 μM. The median lethal concentration difference of these complexes against normal cell lines and cancer cell lines can reach up to 10 times, so it is believed that they have selective killing effect on cancer cell lines.

Among them, the representative complex 1 has significant toxicity to a variety of cancer cell lines, and its median lethal concentration in 24 hours is generally below 2 μM. The median lethal concentration of complex 11 against human malignant melanoma cells is lowest and can be about 70 nM.

Some of the main group metal complexes according to the present invention have stronger fluorescence emission characteristic. Through confocal fluorescence imaging in combination with experimental methods such as protein immunoblotting, mRNA gene chip and proteomics research, the action mechanism of such complexes have been studied. We found that after these complexes enter the cells by passive diffusing, the enzyme activity of the protein disulfide isomerase family in the endoplasmic reticulum is inhibited, the normal protein folding process is hindered, and a series of unfolded protein reactions including endoplasmic reticulum stress are triggered, by which the state and function of mitochondrias are affected, causing the swelling of mitochondrias and the membrane potential of the mitochondrial inner membrane degraded, subsequently, active oxygen species are generated, and ultimately cell homeostasis is destroyed, leading to the cell death. That is obviously different from the cancer cell killing mechanism of platinum-based cancer drugs that target nuclear DNA such as cisplatin.

The main group metal Schiff base complexes according to the present invention have obvious killing effects on cancer cells. It has been demonstrated by experiments that the median lethal concentrations against cancer cell lines in 24 hours of these complexes are significantly lower than those of the main group metal complexes reported in the literatures, even some transition metal complexes with anticancer activity including cisplatin. This means that the complexes according to the present invention have the potential to be used as small molecule anticancer drugs in clinical treatment.

Thus, the present invention further provides a pharmaceutical composition, comprising as an active ingredient the main group metal complex with the structure represented by Formula I or Formula II or the main group metal complex having the structure represented by Formula I or Formula II obtained by the aforementioned preparation method, and pharmaceutically acceptable excipients. The pharmaceutically acceptable salt, solvate, non-covalent compound or prodrug of the main group metal complex having the structure represented by Formula I or Formula II can also be used as the active ingredient of the pharmaceutical composition.

Depending on its administration method, the pharmaceutical composition can be prepared into various forms with a predetermined dosage of the active ingredient, for example, common tablets, capsules, oral solutions, oral emulsions, suppositories, or granules administrated through the gastrointestinal tract. The pharmaceutical composition according to the present invention can also be administered by injection, including intravenous injection, arterial injection, intramuscular injection and spinal cavity injection. By a controlled release manner or via a delivery device, the pharmaceutical composition can be prepared into, for example, common dosage forms, such as injection solution, injection emulsion, injection sustained-release solution, or injection suspension.

According to the application form of the pharmaceutical composition, the excipients in the composition should be inactive ingredients which are applicable to the administration route or way and are non-toxic to the human body.

The excipients can be solid, liquid or gas form. Solid excipients, for example, include sodium chloride, glucose, sodium lactate, poloxamer, sodium lauryl sulfate, sodium dodecylbenzene sulfonate, sodium hydroxide, triethylamine, sodium carbonate, sodium bicarbonate, sucrose, sodium carboxymethyl cellulose, gelatin, xanthan gum, povidone, starch, magnesium stearate, sodium carboxymethyl starch, talc and pectin. Liquid excipients, for example, include ethylene glycol, hydrochloric acid, sulfuric acid, phosphoric acid, acetic acid, triethylamine, water, ethanol, isopropanol, peanut oil, soybean oil, syrup and glycerin. Gas excipients, for example, include carbon dioxide and nitrogen.

The pharmaceutical composition according to the present invention can be a sterile system administrated by injection, wherein the active ingredient with one or more excipients can be prepared as a sterile solution or dispersion system, or prepared as sterile powder which can be converted into a sterile solution for injection immediately before use. It can be prepared by mixing water, ethanol, or appropriate excipients, such as isotonic regulators of blood, surfactants, and antioxidants. The pharmaceutical composition should be stable during preparation and storage. Preferably, the dosage of the active ingredient in the unit dosage form is between 0.01 mg and 10 g, and based on the total weight of the pharmaceutical composition, the active ingredient in the sterile system is 0.01 wt %-10 wt %.

The pharmaceutical composition according to the present invention can be an oral solid, and prepared by mixing the active ingredient and excipients, such as fillers, disintegrants, binders and lubricants and molding by suitable devices.

The pharmaceutical composition can be an oral liquid, and prepared by dissolving or dispersing the active ingredient in a solvent and then mixing with excipients, such as surfactants, thickeners, emulsifiers, preservatives.

In addition to the pharmaceutical compositions in various forms mentioned above, the active ingredient and suitable excipients can also be prepared for local administration, for example, rectal administration, transdermal administration, nasal administration, etc.

The present invention also provides a use of the main group metal complexes having the structure represented by Formula I or Formula II, and pharmaceutically acceptable salt, solvate, non-covalent compound or prodrug thereof, or their pharmaceutical compositions for preparing cancer drugs.

Preferably, they are used for preparing drugs against the cancers including breast cancer, liver cancer, lung cancer, melanoma, prostate cancer, colon cancer, colorectal cancer, glioblastoma, kidney cancer, pancreatic cancer, gastric cancer, lymphoma, cervical cancer, ovarian cancer, esophageal cancer, nasal cancer, leukemia, breast duct cancer, gallbladder cancer, testicular cancer, cardia cancer and thyroid cancer.

Depending on the patient's age, weight, health status, diet, administration route, combination medication, treatment time, etc., the specific dosage of the drug may vary individually. Generally, in the treatment of the above diseases, the dose level of the drug is 0.01-200 mg/kg body weight per day, or 0.5-14 g per patient per day.

The present invention also provides a use of the main group metal complex having the structure represented by Formula I or Formula II, and salt, solvate, non-covalent compound or precursor thereof for optical labeling.

The main group metal complex having the structure represented by Formula I or Formula II has a stronger fluorescence emission, and thus can be prepared as a fluorescent maker to use for fluorescent labeling, especially single and two-photon fluorescent labeling.

It has been found by studies that the complex according to the present invention has a fluorescence color that is significantly different from the autofluorescence color of biological systems. For example, the complex having the structure shown in Example 1 according to the present invention has a red fluorescence emission and the fluorescence quantum yield is up to 50%, which is obviously distinguished from the autofluorescence of biological systems.

Therefore, the main group metal complex having the structure represented by Formula I or Formula II can be used as imaging probes.

Further, in view of the cell level, the main group metal complex according to the present invention with such fluorescence characteristic can be used to study the cell activities, such as cellular location, cellular uptake, and cell physiological changes downstream.

In view of the living organisms, the main group metal complex according to the present invention with such fluorescence characteristic can be used for in vivo imaging. By studying the distribution of the main group metal complex in vivo, targeted drug delivery can be performed much well, so as to deliver the predetermined active ingredient, such as the main group metal complex, and salt, solvate or prodrug thereof, or the main group metal complex together with other ingredients and chemical modifications to the location around the tumor tissue.

In a preferred embodiment, the main group metal complex having the structure represented by Formula I or Formula II can be used to prepare targeted drugs.

In the process of clinical application, it also can be expected to use the main group metal complex with the fluorescence characteristic for drug monitoring, so as to evaluate the effectiveness and individual differences of drugs based on the distribution of drugs in the body.

The main group metal complex having the structure represented by Formula I or Formula II according to the present invention has an excellent light-emitting property, and thereby can also be used as a light-emitting small molecule material in a non-biological system in the fields such as material science, OLED (organic light emitting diode), dye-sensitized solar cells.

EXAMPLES

Example 1

The complex 1 was prepared as follows:

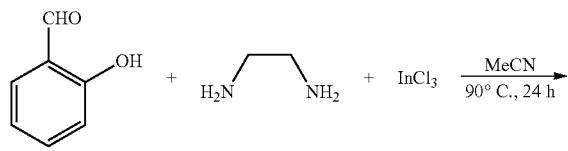

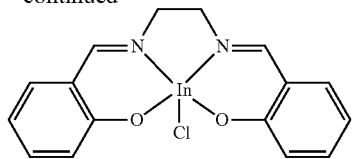

The substituted salicylaldehyde, the diamine precursor and indium trichloride corresponding to complex 1 were placed in acetonitrile, and then reacted at 90° C. under reflux for 24 h. After stopping the reflux, a large amount of ether was added to the system, so that a light yellow solid was precipitated. Then, the precipitated solid was filtered, collected and washed with ether, and consequently the pure complex 1 was yielded.

Characterization

The structure of the complex 1 was characterized by hydrogen nuclear magnetic resonance spectrum, carbon spectrum, high-resolution mass spectrometry and infrared spectroscopy, and the photophysical properties of the complex 1 were characterized by ultraviolet-visible absorption spectrometer and fluorescence spectrometer.

$^1$H NMR (400 MHZ, Methanol-$d_4$) δ 8.12 (s, 2H), 7.70 (m, J=4H), 7.11 (d, J=8.65 Hz, 2H), 6.98 (t, J=7.33 Hz, 2H), 3.91 (s, 2H);

$^{13}$C NMR (101 MHz, Methanol-$d_4$) δ 163.7, 157.8, 132.4, 124.6, 121.4, 116.0, 37.5;

HRMS (ESI+, DMSO, FT-ICR): m/z calcd. for $C_{16}H_{14}InN_2O_2$ ([M-Cl]+) 381.00886, found 381.01022; calcd. for $C_{18}H_{20}InN_2O_3S$ ([M-Cl+DMSO]+) 459.02279, found 459.02408;

FT-IR (KBr pellete, cm$^{-1}$): 1618 (C=N).

Example 2

Complex 2 (Gaa1(s1*s5)): M is gallium, L is acetonitrile, X is —C(CN)=C(CN)—, Y is hydrogen, the modifications on two benzene rings of the salicylaldehyde residue are N-propargyl-N-methylamino and diethylamino at position $R_3$, respectively, and Z is chloride ion.

The complex 2 was prepared as described below.

4-diethylaminosalicylic aldehyde and the maleonitrile diamine precursor were dissolved in acetonitrile with a ratio of 1:1, and subsequently a small amount of sulfuric acid was added dropwisely, and then the system was reacted under reflux at 90° C. for 24 h. After stopping the reflux, a large amount of ether was added to the system, so that a dark purple solid was precipitated. Then, the precipitated solid was filtered, collected and washed with ether, and consequently the intermediate product a. was yielded.

The intermediate product a., 4-N-propargyl-N-methyl-aminosalicylic aldehyde and gallium trichloride were dissolved in acetonitrile with a ratio of 1:1:5, and reacted at 90° C. under reflux for 24 h. After stopping the reflux, a large amount of ether was added to the system, so that a dark red solid was precipitated. Then, the precipitated solid was filtered, collected and washed with ether, and consequently the complex 2 was yielded.

Characterization

The complex 2 was characterized by the same methods as described in Example 1. The results were shown as below:

$^1$H NMR (400 MHZ, DMSO-d6) δ 8.37 (d, J=8.0 Hz, 1H), 8.26 (d, J=7.3 Hz, 1H), 7.58-7.47 (m, 1H), 7.48-7.38 (m, 1H), 6.55 (t, J=8.4 Hz, 1H), 6.47 (t, J=8.9 Hz, 1H), 6.17 (d, J=11.6 Hz, 1H), 6.06 (d, J=12.0 Hz, 1H), 4.34 (s, 2H), 3.50 (q, J=5.4 Hz, 6H), 3.12 (d, J=4.1 Hz, 3H), 1.75 (s, OH), 1.17 (t, J=7.0 Hz, 7H).

Example 3

Complex 3 (Gaa1s1): M is gallium, L is acetonitrile, X is —C(CN)=C(CN)—, Y is hydrogen, the modification on the benzene ring of the salicylaldehyde residue is diethylamino at position R$_3$, and D is chloride ion.

The complex 3 was prepared as described below.

The substituted salicylaldehyde, the diamine precursor and gallium trichloride corresponding to complex 3 were placed in acetonitrile, and then reacted at 90° C. under reflux for 24 h. After stopping the reflux, ether was added to the system, so that a red solid was precipitated. Then, the precipitated solid was filtrated, collected and washed with ether, and consequently the complex 3 was yielded.

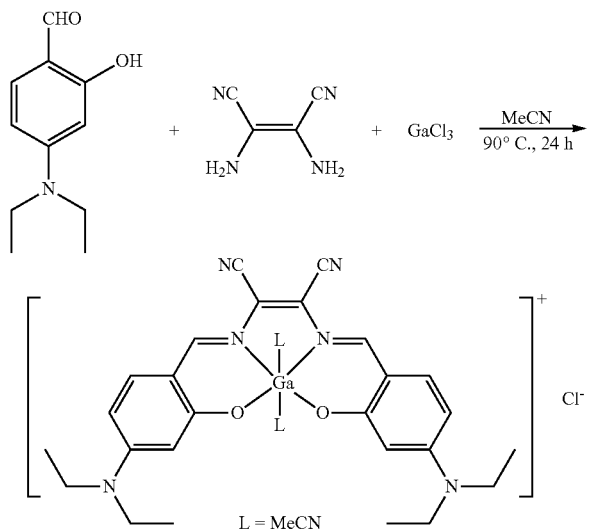

Characterization

The structure of the complex 3 was characterized by hydrogen nuclear magnetic resonance spectrum, carbon spectrum, high-resolution mass spectrometry and infrared spectroscopy, and the photophysical properties of the complex 3 were characterized by ultraviolet-visible absorption spectrometer and fluorescence spectrometer.

$^1$H NMR (400 MHZ, Methanol-d4) δ 8.24 (s, 2H), 7.30 (d, J=9.3 Hz, 2H), 6.53 (dd, J=9.3, 2.5 Hz, 2H), 6.22 (d, J=2.4 Hz, 2H), 3.56 (q, J=7.1 Hz, 8H), 1.26 (t, J=7.1 Hz, 12H);

$^{13}$C NMR (101 MHz, Methanol-d4) δ 172.1, 158.3, 157.9, 139.5, 118.0, 112.1, 111.8, 108.9, 101.6, 46.3, 13.1;

HRMS (ESI+, DMSO, FT-ICR): m/z calcd. for C$_{28}$H$_{32}$GaN$_4$O$_2$ ([M-Cl]+) 525.17756, found 525.17923; calcd. for C30H38GaN2O3S ([M-Cl+DMSO]+) 603.19149, found 603.19322;

FT-IR (KBr pellete, cm$^{-1}$): 1616 (C=N).

Example 4

The complex 11 was prepared as follows:

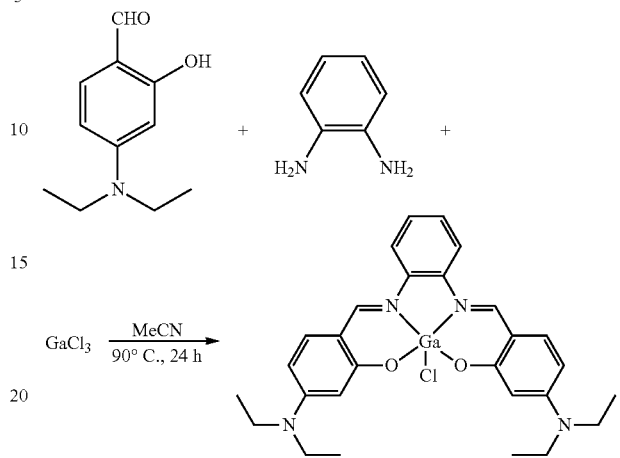

The substituted salicylaldehyde, the diamine precursor and gallium trichloride corresponding to complex 11 were placed in acetonitrile, and then reacted at 90° C. under reflux for 24 h. After stopping the reflux, a large mount of ether was added to the system, so that a yellow solid was precipitated. Then, the precipitated solid was filtrated, collected and washed with ether, and consequently the pure complex 11 was yielded.

Characterization

The structure of the complex 11 was characterized by hydrogen nuclear magnetic resonance spectrum, carbon spectrum, high-resolution mass spectrometry and infrared spectroscopy, and the photophysical properties of the complex 11 were characterized by ultraviolet-visible absorption spectrometer and fluorescence spectrometer.

$^1$H NMR (400 MHZ, Methanol-d$_4$) δ 8.82 (s, 2H), 7.88-7.70 (m, 2H), 7.42-7.14 (m, 4H), 6.38 (dd, J=9.0, 2.5 Hz, 2H), 6.26 (d, J=2.5 Hz, 2H), 3.50 (q, J=7.0 Hz, 8H), 1.24 (t, J=7.0 Hz, 12H);

$^{13}$C NMR (101 MHZ, Methanol-d$_4$) δ 163.7, 158.7, 153.3, 132.8, 128.5, 123.6, 108.0, 104.5, 99.1, 12.9;

HRMS (ESI+, DMSO, FT-ICR): m/z calcd. for C$_{28}$H$_{32}$GaN$_4$O$_2$ ([M-Cl]+) 525.17756, found 525.17923; calcd. for C$_{30}$H38GaN2O3S ([M-C$_1$+DMSO]+) 603.19149, found 603.19322;

FT-IR (KBr pellete, cm$^{-1}$): 1616 (C=N).

Example 5

The complex 5 was prepared as follows:

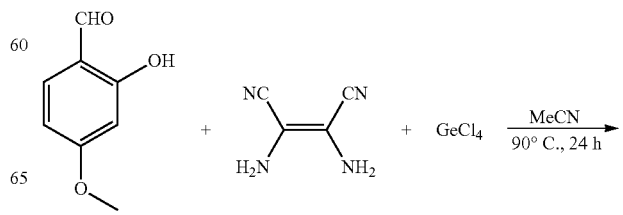

-continued

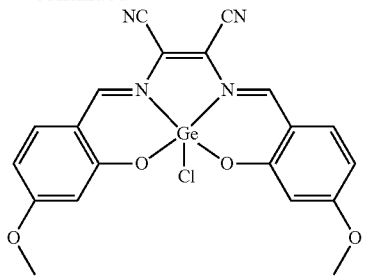

The substituted salicylaldehyde, the diamine precursor and germanium trichloride corresponding to complex 5 were placed in acetonitrile, and then reacted at 90° C. under reflux for 24 h. After stopping the reflux, a large mount of ether was added to the system, so that a red solid was precipitated. Then, the precipitated solid was filtrated, collected and washed with ether, and consequently the pure complex 5 was yielded.

Characterization

The structure of the complex 5 was characterized by hydrogen nuclear magnetic resonance spectrum, carbon spectrum, high-resolution mass spectrometry and infrared spectroscopy, and the photophysical properties of the complex 5 were characterized by ultraviolet-visible absorption spectrometer and fluorescence spectrometer.

$^1$H NMR (400 MHZ, Methanol-$d_4$) δ 8.24 (s, 1H), 7.30 (d, J=9.4 Hz, 4H), 6.53 (dd, J=9.3, 2.4 Hz, 4H), 6.22 (d, J=2.3 Hz, 4H), 3.84 (s, 6H);

$^{13}$C NMR (101 MHz, Methanol-$d_4$) δ 164.3, 163.7, 158.8, 133.4, 125.8, 110.8, 107.0, 102.1, 55.8;

HRMS (ESI+, DMSO, FT-ICR): m/z calcd. for $C_{24}H_{26}GeN_4O_6S_2$ ([M−2Cl+2DMSO]$^+$) 604.05001, found 604.05185;

FT-IR (KBr pellete, cm$^{-1}$): 1620 (C=N).

Example 6

The complexes 4, 6-10, and 12-20 were prepared and characterized by using the same or similar method as described in Examples 1-5. The structures and properties of these complexes were summarized in the following table:

| Complex | Description |
|---|---|
| 6<br>Gaa1s2 | red solid;<br>M is gallium, L is acetonitrile, X is —C(CN)=C(CN)—, Y is hydrogen, the modification on the benzene ring of the salicylaldehyde residue is dimethylamino at position R3, and D is chloride ion.<br>Characterization:<br>$^1$H NMR (400 MHZ, Methanol-d4) δ 8.30 (s, 2H), 7.33 (d, J = 9.3 Hz, 2H), 6.58 (d, J = 9.3 Hz, 2H), 6.23 (d, J = 2.4 Hz, 2H), 3.21 (s, 12H). |
| 7<br>Gaa1s3 | red solid;<br>M is gallium, L is acetonitrile, X is —C(CN)=C(CN)—, Y is hydrogen, the modification on the benzene ring of the salicylaldehyde residue is tetrahydropyrrole substituent at position R3, and D is chloride ion.<br>Characterization:<br>$^1$H NMR (400 MHZ, Methanol-d4) δ 8.24 (s, 2H), 7.29 (d, J = 9.2 Hz, 2H), 6.43 (dd, J = 9.1, 2.3 Hz, 2H), 6.10 (d, J = 2.3 Hz, 2H), 3.64-3.37 (m, 8H), 2.24-1.89 (m, 8H).<br>$^{13}$C NMR (101 MHz, DMSO) δ 170.5, 156.9, 155.6, 111.1, 108.4, 101.0, 48.4, 25.3. |
| 8<br>Gaa1s5 | red solid;<br>M is gallium, L is acetonitrile, X is —C(CN)=C(CN)—, Y is hydrogen, the modification on the benzene ring of the salicylaldehyde residue is N-propargyl-N-methylamino at position R3, and D is chloride ion.<br>Characterization:<br>$^1$H NMR (400 MHZ, DMSO-d6) δ 8.37 (s, 2H), 7.52 (d, J = 9.2 Hz, 2H), 6.55 (dd, J = 9.1, 2.4 Hz, 2H), 6.19 (d, J = 2.4 Hz, 2H), 4.35 (s, 2H), 3.13 (s, 6H), 1.75 (s, 1H). |
| 9<br>Gaa3s1 | yellow solid;<br>M is gallium, L is acetonitrile, X is —C(CN)=C(CN)—, Y is hydrogen, the modification on the benzene ring of the salicylaldehyde residue is diethylamino at position R3, and D is chloride ion.<br>Characterization:<br>$^1$H NMR (400 MHZ, Methanol-d4) δ 8.82 (s, 2H), 7.88-7.70 (m, 2H), 7.44-7.13 (m, 4H), 6.38 (dd, J = 9.0, 2.5 Hz, 2H), 6.26 (d, J = 2.5 Hz, 2H), 3.50 (q, J = 7.0 Hz, 8H), 1.24 (t, J = 7.0 Hz, 12H). |
| 10<br>Gaa1s6 | dark red solid;<br>M is gallium, L is acetonitrile, X is —C(CN)=C(CN)—, Y is hydrogen, the modification on the benzene ring of the salicylaldehyde residue is a fused N-Methylthiomorpholine at position R3/R4, and D is chloride ion.<br>Characterization:<br>$^1$H NMR (400 MHZ, DMSO-d6) δ 8.28 (s, 2H), 7.34 (d, J = 9.3 Hz, 2H), 6.55 (d, J = 9.3 Hz, 2H), 3.91-3.63 (m, 4H), 3.17 (s, 6H), 3.09-2.93 (m, 4H).<br>13C NMR (101 MHz, DMSO) δ 163.8, 157.6, 152.0, 134.9, 130.2, 117.2, 110.2, 107.4, 105.8, 52.5, 41.0, 22.9. |
| 4<br>Gaa1s0 | dark red solid;<br>M is gallium, L is acetonitrile, X is —C(CN)=C(CN)—, Y is hydrogen, there is no modification on the benzene ring of the salicylaldehyde residue, and D is chloride ion.<br>Characterization:<br>$^1$H NMR (400 MHz, Methanol-d4) δ 8.93 (s, 2H), 7.76 - 7.62 (m, 4H), 7.11 (d, J = 8.6 Hz, 2H), 6.98 (t, J = 7.4 Hz, 2H). |

| Complex | Description |
|---|---|
| 12<br>Gaa1s9 | dark red solid;<br>M is gallium, L is acetonitrile, X is —C(CN)=C(CN)—, Y is hydrogen, the modification on the benzene ring of the salicylaldehyde residue is a fused N-Methylthiomorpholine at position R2/R3, and D is chloride ion.<br>Characterization:<br>$^1$H NMR (400 MHZ, Methanol-d4) δ 8.23 (s, 2H), 7.15 (s, 2H), 6.28 (s, 2H), 5.49 (s, 2H), 3.90-3.79 (m, 4H), 3.18 (s, 4H), 3.06-2.95 (m, 6H). |
| 13<br>Gaa1snBu | dark red solid;<br>M is gallium, L is acetonitrile, X is —C(CN)=C(CN)—, Y is hydrogen, the modification on the benzene ring of the salicylaldehyde residue is N-n-butyl-N methylamino at position R3, and D is chloride ion.<br>Characterization:<br>$^1$H NMR (400 MHZ, Chloroform-d) δ 8.14 (s, 2H), 7.07 (d, J = 9.2 Hz, 2H), 6.34 (dd, J = 9.3, 2.4 Hz, 2H), 6.26 (d, J = 2.4 Hz, 2H), 3.29-3.45 (m, 8H), 1.60-1.68 (m, 8H), 1.46-1.26 (m, 8H), 0.98 (t, J = 7.2 Hz, 12H). |
| 14<br>Gaa3s0 | yellow solid;<br>M is gallium, L is acetonitrile, X is ortho-disubstituted benzene, Y is hydrogen, there is no modification on the benzene ring of the salicylaldehyde residue, and D is chloride ion.<br>Characterization:<br>1H NMR (400 MHZ, Methanol-d4) δ 9.37 (s, 2H), 8.13 (dd, J = 6.3, 3.4 Hz, 2H), 7.65 (dd, J = 8.0, 1.8 Hz, 2H), 7.63-7.53 (m, 4H), 7.10 (dd, J = 8.6, 1.1 Hz, 2H), 6.92 (ddd, J = 8.0, 7.0, 1.1 Hz, 2H). |
| 15<br>Gaa7s1 | orange solid;<br>M is gallium, L is acetonitrile, X is 3,4-disubstituted pyridine, Y is hydrogen, the modification on the benzene ring of the salicylaldehyde residue is diethylamino at position R3, and D is chloride ion.<br>Characterization:<br>1H NMR (400 MHZ, Chloroform-d) δ 8.96 (d, J = 13.8 Hz, 2H), 8.86 (s, 1H), 8.33 (d, J = 5.6 Hz, 1H), 7.77 (d, J = 5.7 Hz, 1H), 7.35 (t, J = 8.1 Hz, 2H), 6.47 (dd, J = 19.1, 9.0 Hz, 2H), 6.25 (d, J = 3.0 Hz, 2H), 3.54 (p, J = 7.4 Hz, 8H), 1.26 (td, J = 7.0, 3.6 Hz, 12H). |
| 16<br>Gaa7s3 | orange solid;<br>M is gallium, L is acetonitrile, X is 3,4-disubstituted pyridine, Y is hydrogen, the modification on the benzene ring of the salicylaldehyde residue is a tetrahydropyrrole substituent at position R3, and D is chloride ion.<br>Characterization:<br>1H NMR (400 MHZ, Chloroform-d) δ 9.01 (s, 1H), 8.86 (d, J = 12.8 Hz, 2H), 8.41 (d, J = 6.6 Hz, 1H), 8.10 (d, J = 6.6 Hz, 1H), 7.36 (dd, J = 14.8, 9.1 Hz, 2H), 6.54 (d, J = 9.3 Hz, 1H), 6.42 (d, J = 9.1 Hz, 1H), 6.11 (d, J = 2.3 Hz, 2H), 3.57 (d, J = 46.4 Hz, 8H), 2.10 (d, J = 6.5 Hz, 8H). |
| 17<br>Gaa0s1 | light yellow solid;<br>M is gallium, L is acetonitrile, X is —CH$_2$—CH$_2$—, Y is hydrogen, the modification on the benzene ring of the salicylaldehyde residue is diethylamino at position R3, and D is chloride ion.<br>Characterization:<br>1H NMR (400 MHZ, Chloroform-d) δ 9.01 (s, 1H), 8.86 (d, J = 12.8 Hz, 2H), 8.41 (d, J = 6.6 Hz, 1H), 8.10 (d, J = 6.6 Hz, 1H), 7.36 (dd, J = 14.8, 9.1 Hz, 2H), 6.54 (d, J = 9.3 Hz, 1H), 6.42 (d, J = 9.1 Hz, 1H), 6.11 (d, J = 2.3 Hz, 2H), 3.57 (d, J = 46.4 Hz, 8H), 2.10 (d, J = 6.5 Hz, 8H). |
| 18<br>Gaa4s1 | orange solid;<br>M is gallium, L is acetonitrile, X is 4-cyano ortho-disubstituted benzene, Y is hydrogen, the modification on the benzene ring of the salicylaldehyde residue is diethylamino at position R3, and D is chloride ion.<br>Characterization:<br>1H NMR (400 MHZ, DMSO-d6) δ 8.92 (d, J = 9.7 Hz, 2H), 8.34 (d, J = 1.7 Hz, 1H), 7.99 (d, J = 8.7 Hz, 1H), 7.69 (dd, J = 8.6, 1.6 Hz, 1H), 7.33 (dd, J = 12.8, 9.1 Hz, 2H), 6.40 (ddd, J = 8.6, 5.6, 2.4 Hz, 2H), 6.04 (d, J = 2.4 Hz, 2H), 1.17 (t, J = 7.0 Hz, 12H). |
| 19<br>Gaa5s1 | orange solid;<br>M is gallium, L is acetonitrile, X is 4,5-dicyano ortho-disubstituted benzene, Y is hydrogen, the modification on the benzene ring of the salicylaldehyde residue is diethylamino at position R3, and D is chloride ion.<br>Characterization:<br>1H NMR (400 MHZ, DMSO-d6) δ 8.95 (s, 2H), 8.52 (s, 2H), 7.31 (d, J = 9.1 Hz, 2H), 6.45 (dd, J = 9.2, 2.4 Hz, 2H), 6.03 (s, 2H), 3.49 (q, J = 7.0 Hz, 8H), 1.18 (t, J = 7.0 Hz, 12H). |
| 20<br>Gaa1s8 | orange solid;<br>M is gallium, L is acetonitrile, X is —C(CN)=C(CN)—, Y is hydrogen, the modification on the benzene ring of the salicylaldehyde residue is a fused 3,3-dimethylcyclohexane at position R2/R3 and position R3/R4, and D is chloride ion.<br>Characterization:<br>1H NMR (400 MHZ, Chloroform-d) δ 8.10 (s, 2H), 7.04 (s, 2H), 3.51 (t, J = 6.2 Hz, 4H), 3.39 (t, J = 5.8 Hz, 4H), 1.79 (t, J = 5.9 Hz, 4H), 1.74 (t, J = 6.3 Hz, 4H), 1.65 (s, 12H), 1.28 (s, 12H). |

EXPERIMENTS

Experiment 1

Activity Test Experiment and Results for the Complexes:

The cell lines used in the experiment were obtained from Peking University. The cells were cultured in a cell incubator containing 5% $CO_2$ under the atmosphere of saturated steam at a constant temperature of 37° C. The medium used was a high-sugar Dulbecco's modified Eagle's medium containing 10% fetal bovine serum, 100 μg/mL penicillin and 100 U/mL streptomycin. The cells were grown in a six-well culture plate and passaged every other day. The cytotoxicity of the complex was evaluated by the CCK-8 kit, in which the cells were passed to a 96-well plate containing about 25,000 of cells and 200 μL of medium in each well. After the cells had grown stably and adherently, the medium was changed to complete mediums with different concentrations of the complex to be detected, and a 3-well parallel experiment was performed for each concentration. After culturing in the incubator for 24 hours, the medium was removed and the cells were washed with 100 μL of PBS buffer (pH=7.4) for 3 times. Subsequently, 100 μL mixture of 10% CCK-8 solution and 90% serum-free medium was added into both the test wells and the control wells, and then was placed in an incubator for culturing. After about 1 hour, the absorption of 450 nm wavelength light in the test and control wells were measured by using a microplate reader, and the cell viabilities (CV) under different concentrations of the complex were calculated according to the following formula:

$$CV = \frac{A_s - A_b}{A_c - A_b} \times 100\%$$

in which A is the absorption value of 450 nm wavelength light; the subscript s represents the well to be tested with sample, c represents the live cell control well without sample, and b represents the blank control well without sample and cells. A cytotoxicity curve based on the obtained cell viabilities under different concentrations of the complex was drawn, and the median lethal concentration $IC_{50}$ of the complex against the cell line then could be read out from the drawing.

Figure 2:
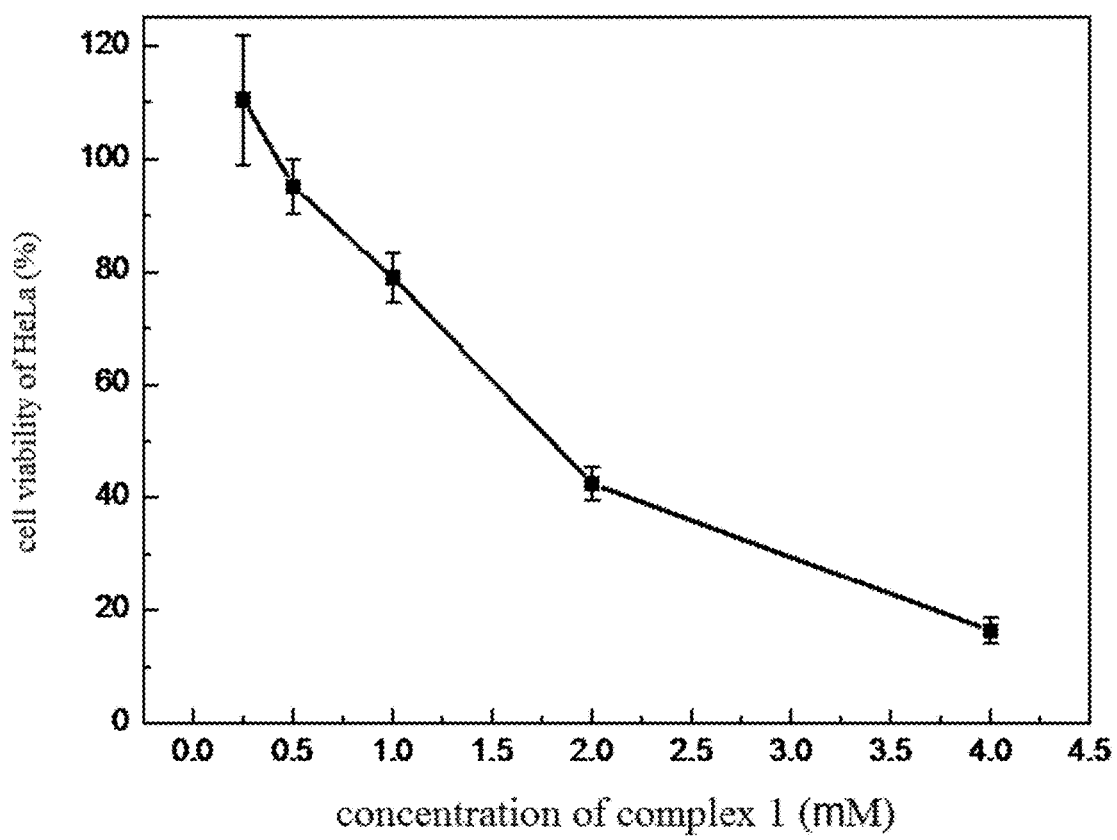
FIG. 2 shows the cytotoxicity curve of the complex against the human cervical cancer cell line HeLa according to Experiment 1.

By the aforementioned method, the toxicity of the complexes against HeLa cell line were preliminarily screened. The cytotoxicity curve of the complex 1 against the human cervical cancer cell line HeLa was shown in FIG. 2. Then, the experiments about the toxicity selectivity of the complexes among multi-cell lines were performed. The results were shown in FIG. 1, in which A375 was a human malignant melanoma cell line, A549 was a human non-small cell lung cancer cell line, SW480 was a human colorectal cancer cell line, and MCF7 was an in situ ER-positive human breast cancer cell line. It could be seen from FIG. 1 that the median lethal concentrations of the complexes 1, 11 and 5 in 24 hours against different cell lines were at the level of 0.1 nM to 2 μM, which demonstrated that these complexes have obvious killing effect against the cancer cells.

Meanwhile, the complex 3 (3 #) prepared in Example 3 and cisplatin were subjected to the control experiments about the toxicity selectivity among multi-cell lines by the above method. The cell lines used were Hela, HepG2 liver cancer cell lines, A375, MCF7, MOLT-4 acute lymphoblastic leukemia cells, MDA-MB-231 highly metastatic breast cancer cell line, A549, HEK293 human renal epithelial cell line, COS7 renal epithelial cells, DU145 prostate cancer cells, Raw264.7 monocyte giant Phages. The results were shown in Table 1 (in vitro Cytotoxicity of 3 and cisplatin against different cell lines) below.

TABLE 1 in vitro Cytotoxicity of 3 and cisplatin against different cell lines

| | $IC_{50}{}^a/\mu M$ | | | | | |
|---|---|---|---|---|---|---|
| | HeLa | HepG2 | A375 | MCF7 | MOLT-4 | MDA-MB-231 |
| 3# | 1.6 ± 0.1 | 1.3 ± 0.5 | 1.2 ± 0.3 | 2.7 ± 0.5 | 0.9 ± 0.1 | 5.2 ± 0.9 |
| cisplatin | 5.3 ± 0.3 | 5.3 ± 0.1 | 3.4 ± 0.3 | 9.1 ± 0.9 | 2.0 ± 0.2 | 27.0 ± 1.3 |
| | A549 | DU145 | | HEK293 | COS7 | Raw264.7 |
| 3# | 0.8 ± 0.1 | 0.8 ± 0.1 | | 0.7 ± 0.1 | 1.6 ± 0.6 | 3.2 ± 0.1 |
| cisplatin | 9.4 ± 1.5 | 2.7 ± 0.1 | | 2.0 ± 0.1 | 6.7 ± 0.6 | 10.1 ± 1.2 |

It could be seen from Table 1 that, the median lethal concentration of the complex 3 in 24 hours against different cell lines were at the level of 0.1 nM to 2 μM, which demonstrated that the complex 3 has obvious killing effect against the cancer cells compared to cisplatin.

Experiment 2

Cell Culture and Measurement of Cytotoxicity

The cell lines used in the experiments were obtained from Peking University. The cells were cultured in a cell incubator containing 5% $CO_2$ under the atmosphere of saturated steam at a constant temperature of 37° C. The medium used was a high-sugar Dulbecco's modified Eagle's medium containing 10% fetal bovine serum, 100 μg/mL penicillin and 100 U/mL streptomycin. The cells were grown in a six-well culture plate and passaged every other day. The cytotoxicity of the complex was evaluated by the CCK-8 kit, in which the cells were passed to a 96-well plate containing about 25,000 of cells and 200 μL of medium in each well. After the cells had grown stably and adherently, the medium was changed to complete mediums with different concentrations of the complex to be detected, and a 3-well parallel experiment was performed for each concentration. After culturing in the incubator for 24 hours, the medium was removed and the cells were washed with 100 μL of PBS buffer (pH=7.4) for 3 times. Subsequently, 100 μL mixture of 10% CCK-8 solution and 90% serum-free medium was added into both the test wells and the control wells, and then was placed in an incubator for culturing. After about 1 hour, the absorption of 450 nm wavelength light in the test and control wells were measured by using a microplate reader, and the cell viabilities (CV) under different concentrations of the complex were calculated according to the following formula:

$$CV=(A_s-A_b)/(A_c-A_b)\times 100\%$$

in which A is the absorption value of 450 nm wavelength light; the subscript s represents the well to be tested with sample, c represents the live cell control well without sample, and b represents the blank control well without sample and cells. Based on the obtained cell viabilities under different concentrations of the complex in Examples 1-6, A cytotoxicity curve was drawn, and the median lethal concentration $IC_{50}$ of the complex against the cell line then could be read out from the drawing.

The safety index (SI) was calculated according to the following equation:

$$^b\text{Safety Index (SI)}=IC_{50}\text{ (HUVEC)}/IC_{50}\text{ (Hela)}$$

The cell lines used were HeLa, HepG2, MCF7, SW480, A375, A549, normal colonic epithelial cells NCM460, human microglia CHEM5 and human umbilical vein endothelial cells HUVEC.

The results were shown in Table 2 (In vitro anticancer activities of complexes) below.

TABLE 2

In vitro anticancer activities of complexes.[a]

| Complex | $IC_{50}(\mu M)$ | | | | | | | | | $SI^b$ |
| --- | --- | --- | --- | --- | --- | --- | --- | --- | --- | --- |
| | Hela | HepG 2 | MCF7 | SW480 | A375 | A549 | NCM460 | CHEM5 | HUVEC | |
| 1# | 17.23 | 29.54 | 46.79 | 26.67 | 11.11 | 27.19 | 87.23 | 52.05 | 114.98 | 6.37 |
| 5# | 39.17 | 48.21 | 181.79 | 68.99 | 36.12 | 50.92 | 134.37 | 169.38 | 187.38 | 4.78 |
| 3# | 0.70 | 1.25 | 0.42 | 1.13 | 0.30 | 0.16 | 0.55 | 0.87 | 1.32 | 1.89 |
| 13# | 21.48 | 20.87 | 1.74 | 4.10 | 0.90 | 2.72 | 20.61 | 2.28 | 3.50 | 0.16 |
| 14# | 19.53 | 38.64 | 53.00 | 257.49 | 23.97 | 76.47 | 211.88 | 65.12 | 162.76 | 8.33 |
| 10# | 87.67 | 72.65 | 61.72 | 451.41 | 91.19 | 124.15 | 321.90 | 51.87 | 332.39 | 3.79 |
| 9# | 12.36 | 46.15 | 34.78 | 4.89 | 1.37 | 1.22 | 33.45 | 1.81 | 9.33 | 0.75 |
| 8# | 259.81 | 291.42 | 190.18 | 572.17 | 228.60 | 138.82 | 71.02 | 236.34 | 203.07 | 0.78 |
| 4# | 75.29 | 43.49 | 134.36 | 0.59 | 2.20 | 1.16 | 27.66 | 1.64 | 6.37 | 0.08 |
| 6# | 1.38 | 7.75 | 0.47 | 4.85 | 0.07 | 1.38 | 6.44 | 2.27 | 4.09 | 0.64 |
| 11# | 0.97 | 0.92 | 0.24 | 4.10 | 0.67 | 2.72 | 1.72 | 0.82 | 1.38 | 1.42 |
| 12# | 45.82 | 34.55 | 43.51 | 42.60 | 10.82 | 39.28 | 89.87 | 44.66 | 58.90 | 1.29 |
| 2# | 6.35 | 8.19 | 5.29 | 2.20 | 0.83 | 2.29 | 4.26 | 2.82 | 1.88 | 0.30 |
| 7# | 8.61 | 10.30 | 14.20 | 7.58 | 1.40 | 3.56 | 23.08 | 5.71 | 2.47 | 0.30 |
| 15# | 97.42 | 89.67 | 203.82 | 324.71 | 214.64 | 272.87 | 339.56 | 298.49 | 75.78 | 0.78 |

[a]$IC_{50}$ was measured by method of MTT.

It can be seen that, a plurality of complexes show the anti-cancer activity against different cancer cell lines, and among them, 3 # and 11 # complexes show the greatest anti-cancer activity against many cancer cell lines, with $IC_{50}$ values much lower than other complexes. In addition, the safety indexes of 3 # and 11 # complexes against HUVEC cells were 1.89 and 1.42, respectively, and that is to say, they had lower cytotoxicity to normal cells. The results showed that 3 # and 11 # complexes have significant applicability in cancer treatment.

Experiment 3

Cell Imaging Experiment

The instrument used for living cell fluorescence imaging is Nikon AIR-si laser scanning confocal fluorescence microscope (Japan). The cells were transplanted and attached on a round cover glass treated with 0.1 mM polylysine, and then placed in a complete medium to be cultured for 24 hours. After that, the cells were treated with a sample of the complex to be tested. The treated living cell sample was rinsed twice with phosphate buffer solution and then placed under a microscope for imaging. Instrument parameters were as follows: the objective lens was a 60× oil lens, the imaging resolution was 1024×1024, and the scanning speed was 0.5 frames per second. Excitation light and detectors with different wavelengths were used for detection during imaging.

Particularly, the complex 3 prepared in Example 3, 488 nm laser excitation, and 585/65 detector channel were used.

Figure 3:
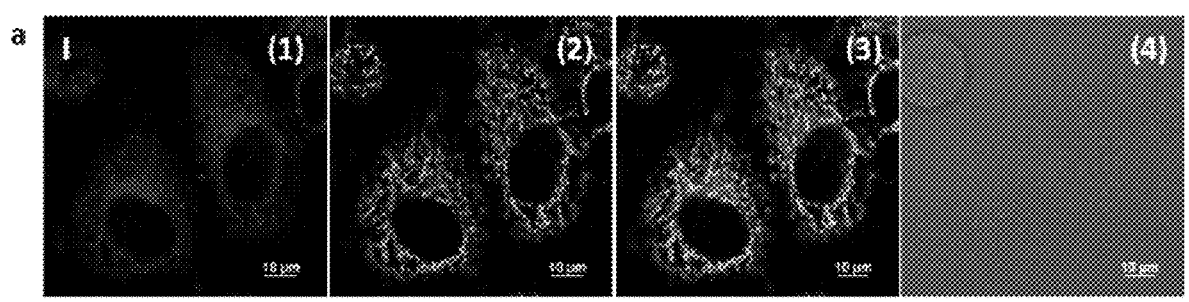
FIG. 3 shows the cell imaging diagram according to Experiment 3.

The results were shown in FIG. 3. FIG. 3(1) was a fluorescence distribution diagram of the complex 3 in the cells, FIG. 3(2) was a fluorescence distribution diagram of the commercially available mitochondria labeling, FIG. 3(3) was the overlapped diagram of FIG. 3(1) and FIG. 3(2), and FIG. 3(4) was an image of cells without fluorescence distribution. It can be seen that the complex 3 was mainly distributed in mitochondria of the cells, and when accumulating on tumor sites, it was also distributed in mitochondria of the tumor cells.

Experiment 4

In Vivo Experiments in Mice
In Vivo Fluorescence Experiment:

HeLa $(1.5\times 10^6)$ was transplanted around the hip joint of 6-week-old male nude mice to form transplanted tumors. After the tumors had grown up to about 200 mm$^3$, the dosing solutions of the complex 3 (3 #) in Example 3 and the complex 11 (11 #) in Example 4 with different concentrations prepared by adding saline were injected into the mice through tail vein with a dosage of 1.4-6.4 mg/kg. At multiple points during a period from 5 minutes to 72 hours after the injection, in vivo imaging was performed to observe the distribution of the complex 3 in mice and the location of tumors. The instrument used was in vivo imaging system of Xenogen (Caliper Life Sciences, Hopkinton, MA, USA), with the imaging parameters of 500 nm excitation and 560-620 detector channel. After 72 hours, the nude mice was dissected, and the main organs were taken out and placed under the imaging system for imaging using the same parameters to observe the distribution of the complexes in each organ.

Figure 4:
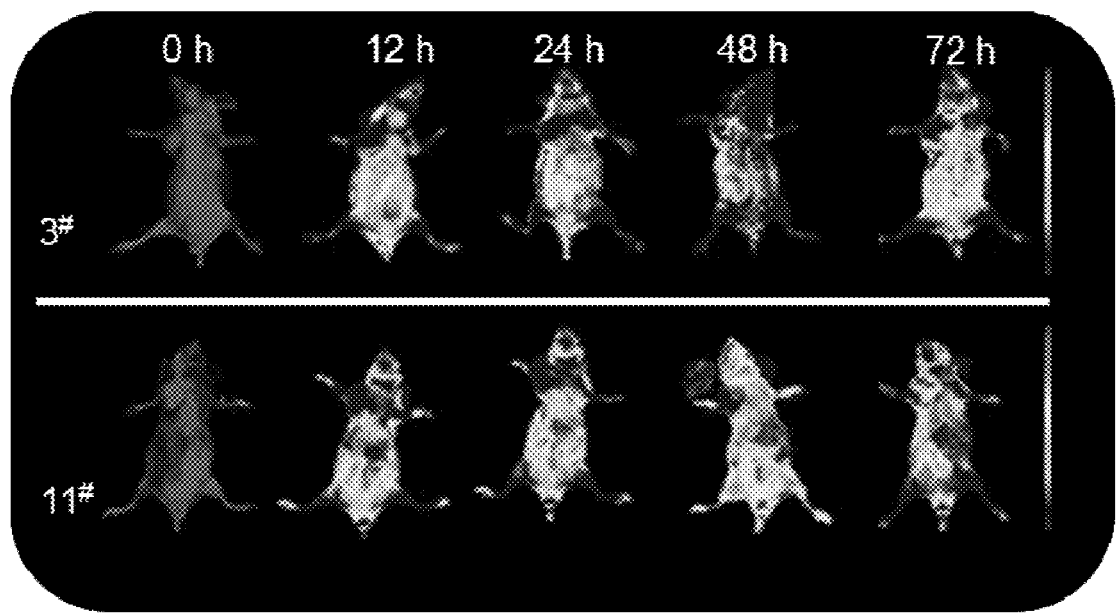
FIG. 4 shows the fluorescence image obtained in the mouse in vivo experiment according to Experiment 4.
Figure 4:
Figure 4:

As shown in FIG. 4A, still a lot of the complex 3 and the complex 11 accumulated in the tumor tissue 72 hours after the injection. FIGS. 4B and 4C showed the accumulation of complexes in the major organs, i.e., heart, liver, spleen, lung and kidney, and it can be seen that, the accumulation of the complex 3 # and the complex 11 # in the liver was much higher than that in other organs, and in contrast, there was almost no accumulation in the heart and the spleen.

Additionally, the concentration of the complex 3 # or 11 # in the major organs was measured by ICP-MS (inductively coupled plasma mass spectrometer). The concentrations of 3 # and 11 # complexes in tumor tissues were 8.84 and 9.55 µg/g, respectively, which were higher than those in the heart, spleen, lung and kidney, indicating that the complexes could accumulate in tumor tissues, which was consistent with the fluorescence images.

Experiment 5

In Vivo Tumor Suppression Experiment:

Nude mice carrying HeLa tumors were divided into 4 groups, each with 8 mice. After growing up to about 200 mm³, the tumors were treated with cisplatin, the complex 3 prepared in Example 3, and the complex 11 prepared in Example 4, respectively, to set a tumor control group. The dosage was 4 µmol/kg, and the administration frequency was once every 2 days. The volume of the tumor was calculated with the length and width of the tumor according to the following formula:

$$\text{Tumor volume}(\text{mm}^3) = \frac{1}{2} \times \text{length} \times \text{width}^2.$$

After 21 days, the nude mice of each group were died and dissected. The tumor inhibition was calculated according to the following formula:

$$\text{Tumor inhibition} = \frac{Wc - Wt}{Wc} \times 100\%$$

in which Wc and Wt were the masses of the tumors in the control group and the experimental group, respectively.

Figure 5:
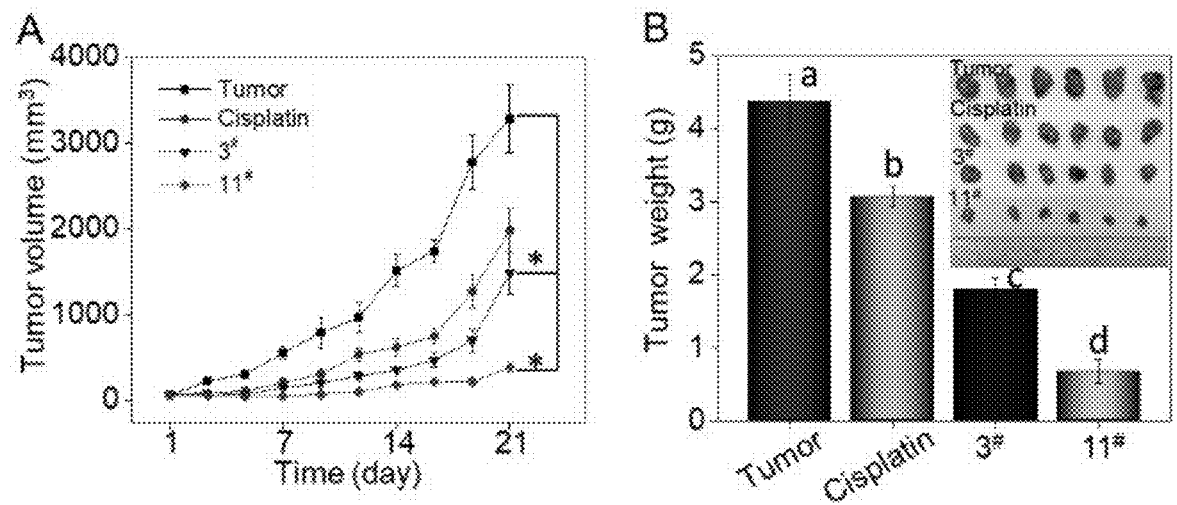
FIG. 5 show the changes in volume and mass of the tumor after treatment in the in vivo tumor suppression experiment according to Experiment 5, respectively.

The curves about the changes of the tumor volume and mass after treatment were shown in FIGS. 5A and 5B. It can be seen that the therapeutic effect of the complex 11 # was better than that of the complex 3 #. The volume and mass of the tumor after treated with the complex group were always smaller than those treated with the cisplatin group. That is to say that, the experimental group was better than the control group.

Figure 7:
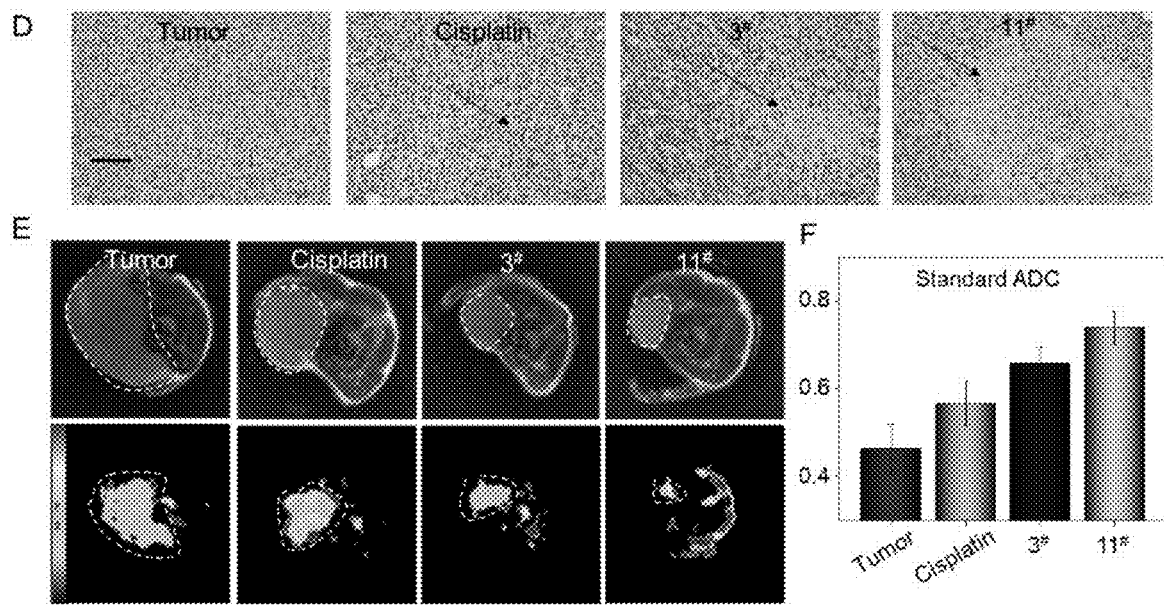
FIG. 7 shows the H&E staining diagram of tumor tissue (D) in the in vivo tumor suppression experiment according to Experiment 5; black and white NMR image and color NMR image of tumor location in each experimental group (E); the standard deviation of the tumor tissue change (F) in each group of E.

As shown in FIGS. 7D, 7E and 7F, free complexes 3 # and 11 # significantly inhibited the growth of tumors. After 21 days of treatment, the tumor inhibitions of the complexes 3 # and 11 # were 56.8% and 84.6%, respectively. The tumor inhibition of cisplatin was 29.9%. The results showed that the free gallium complexes 3 # and 11 # have better anti-tumor effects than that of free cisplatin.

Figure 6:
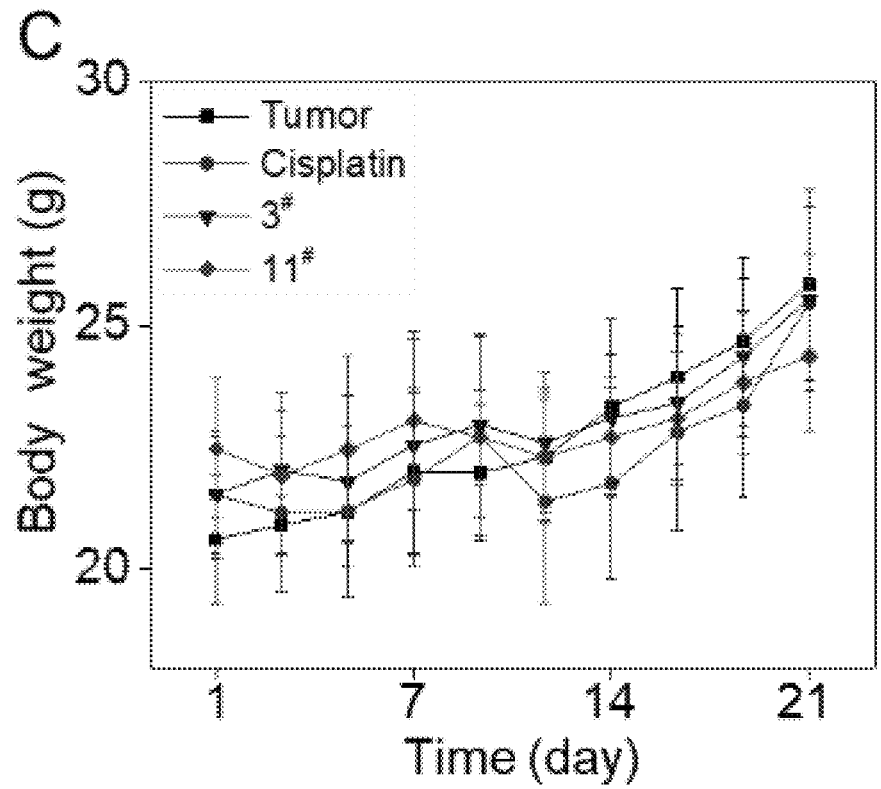
FIG. 6 shows the weight change curve of nude mice after treatment in the in vivo tumor suppression experiment according to Experiment 5.

Meanwhile, it can be seen from FIG. 6 that the weight of nude mice did not change significantly during the treatments in all of the groups, indicating that these treatments could be tolerated very well and there was no any acute side effects occurred during the treatments.

Additionally, the histological changes of tumor tissues were checked by H&E staining. As shown in FIGS. 7D, tumor tissues showed different degrees of necrosis after treatments, and the treatment effects of the complexes were better than that of cisplatin.

The blood samples were collected for hematological analysis to study the effects of cisplatin and the complexes 3 # and 11 # on liver and kidney function of nude mice. The research indicators included alanine aminotransferase (ALT), urea nitrogen (BUN), triglycerides (TG), creatine kinase (CK), aspartate aminotransferase (AST), creatinine (CREA), high Density lipoprotein (HDLC), and lactate dehydrogenase (LDH).

Figure 8:
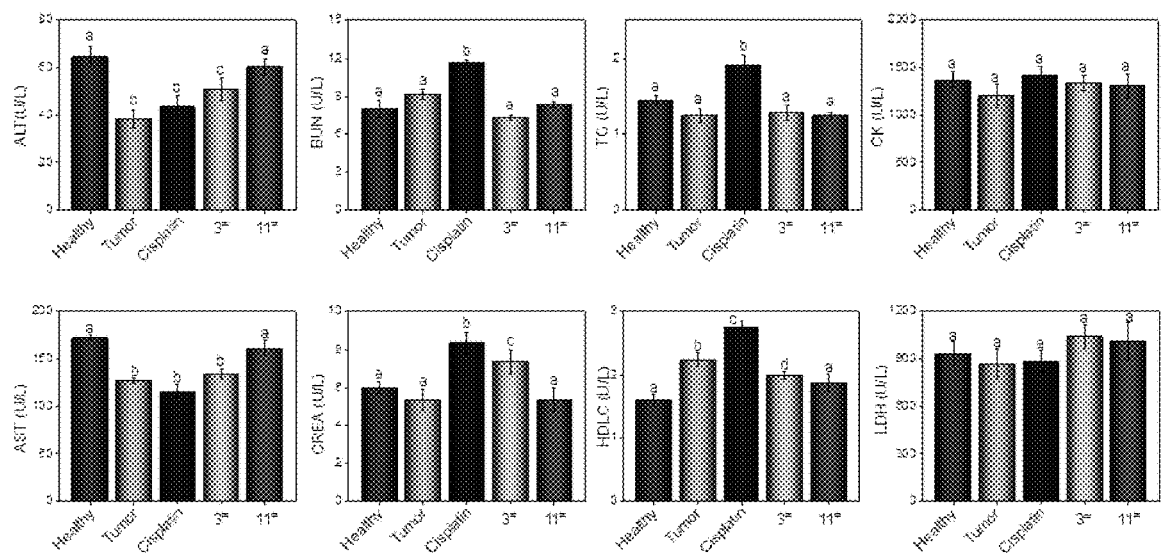
FIG. 8 shows the results of hematological analysis in the in vivo tumor suppression experiment according to Experiment 5.

The kidney function was related to the blood indicators of BUN and CREA and the liver function. The results about alanine aminotransferase (ALT) and aspartate aminotransferase (AST) in the blood of nude mice were shown in FIG. 8. As shown, cisplatin could cause the acute toxicity against the liver and the kidney, and in contrast, the complexes 3 # and 11 # could significantly reduce the damage of cisplatin or tumors to the kidney and liver function, so that the blood biochemical indicators returned to the health level.

Further, the parts such as heart, spleen, lung, liver, and kidney were subjected to the H&E staining analysis.

Figure 9:
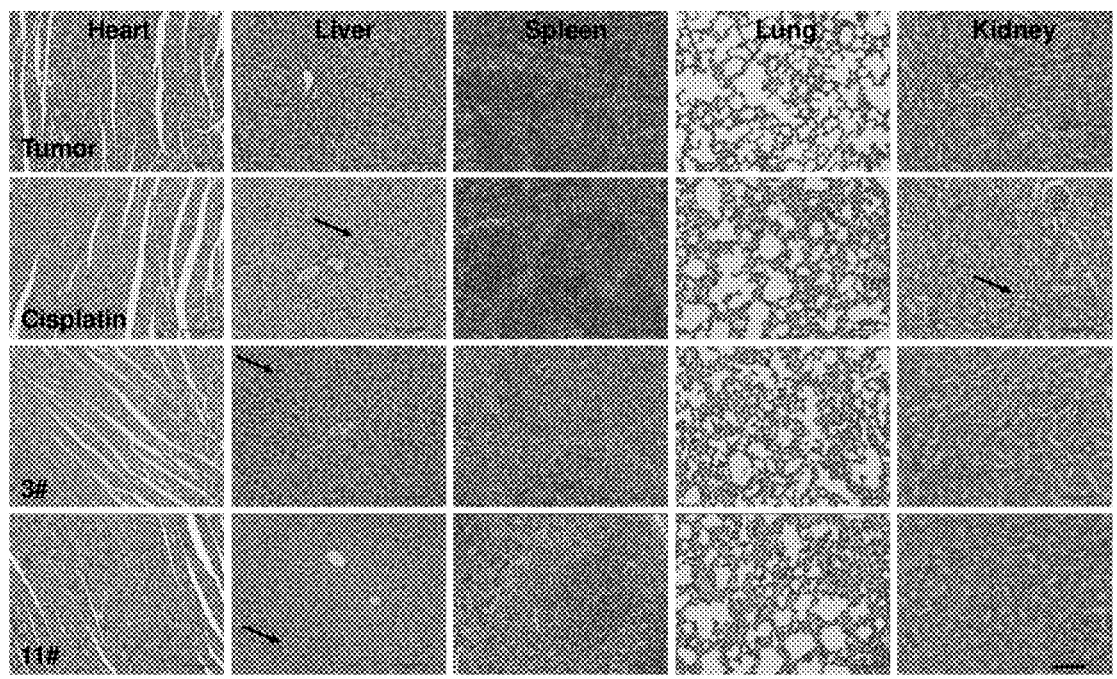
FIG. 9 shows the H&E staining image of major organs in the in vivo tumor suppression experiment according to Experiment 5.

As shown in FIG. 9, under the experimental conditions, no significant pathological changes were found in the heart, spleen and lungs. However, liver edema and degeneration and kidney swelling were observed in the cisplatin treatment group. In contrast, in the complexes 3 # and 11 # groups, no damage of kidney and only slight damage of liver occurred. The results indicated that the potential toxic side effects of the complexes were lower than that of cisplatin.

These results further confirm that the gallium complexes 3 # and 11 # have higher safety and application potential than cisplatin.

The present invention has been described in detail in combination with the embodiments and the examples above, but these descriptions should not be understood as the limits to the present invention. Those skilled in the art should understand that, without departing from the spirit and scope of the present invention, various equivalent substitutions, modifications or improvements can be made to the technical solutions of the present invention and its embodiments, and all of these fall within the scope of the present invention. The protection scope of the present invention is subject to the appended claims.

What is claimed is:

1. A main group metal compound is selected from the group consisting of

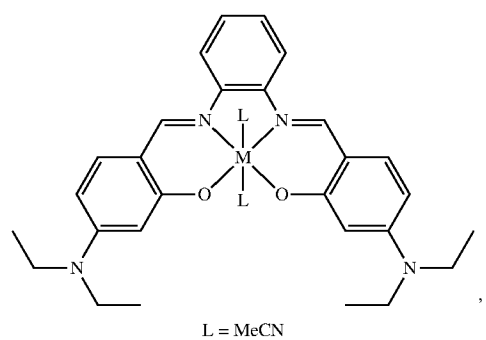

L = MeCN

-continued
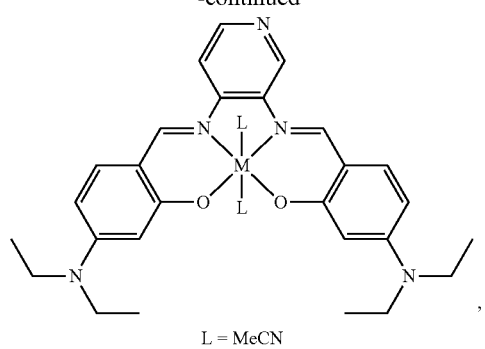
L = MeCN
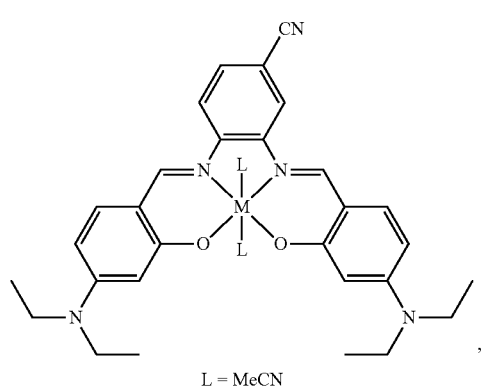
L = MeCN
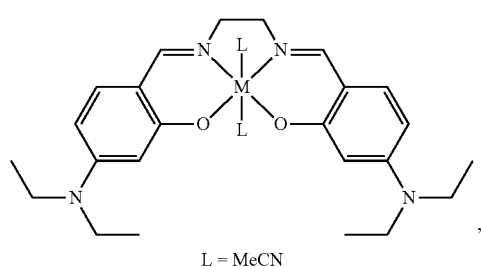
L = MeCN
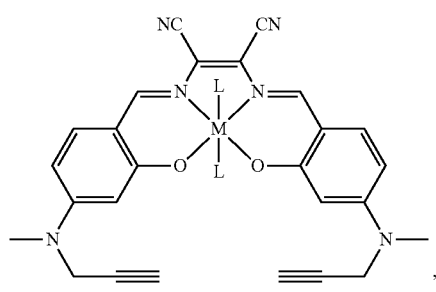
L = MeCN
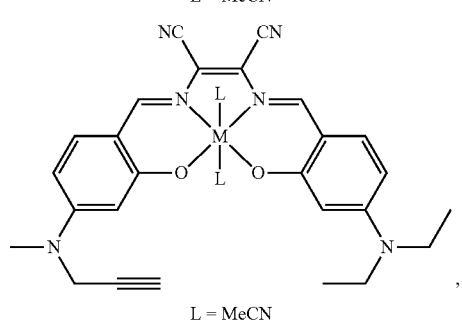
L = MeCN
-continued
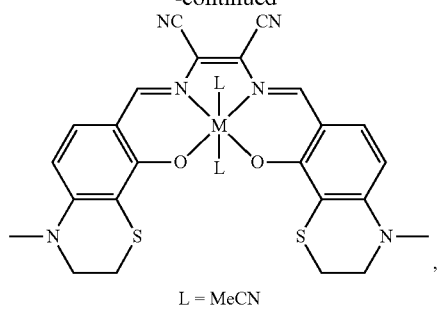
L = MeCN
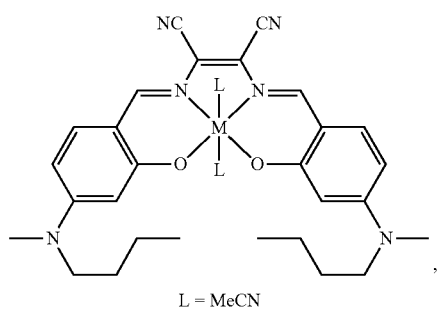
L = MeCN
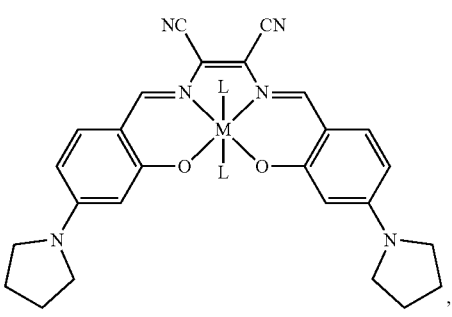
L = MeCN
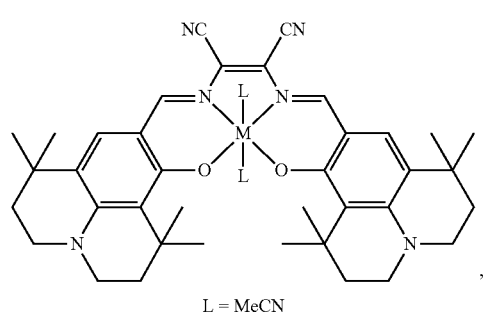
L = MeCN
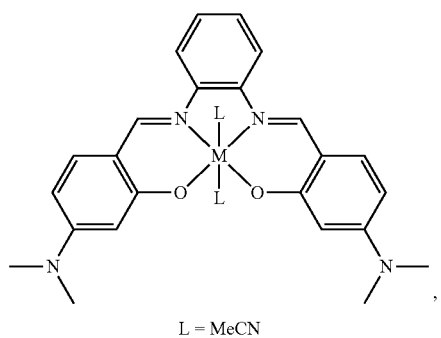
L = MeCN

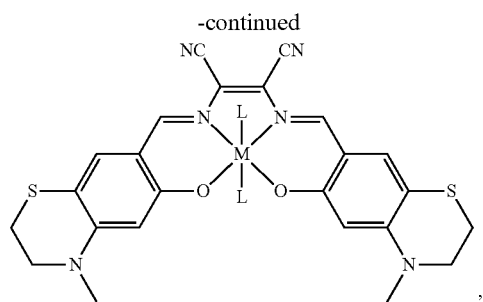

L = MeCN

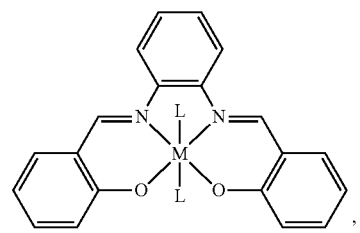

L = MeCN

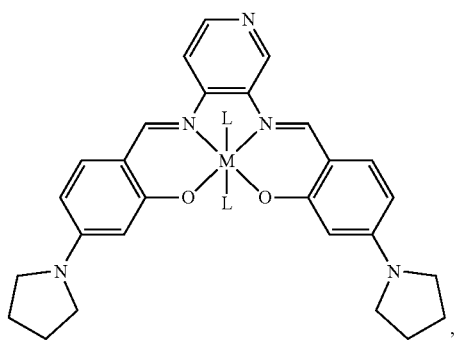

L = MeCN

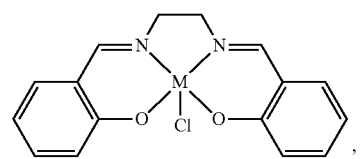

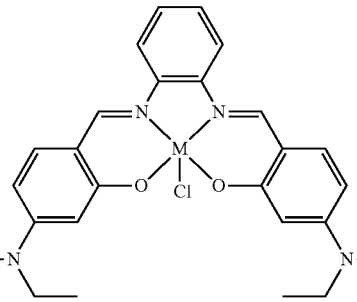

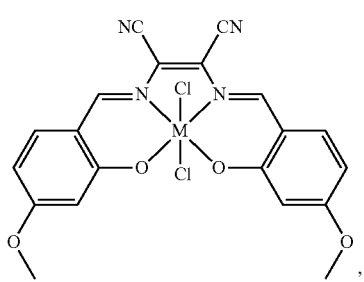

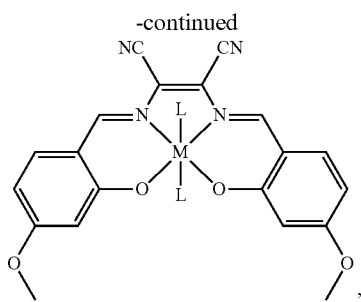

L = MeCN

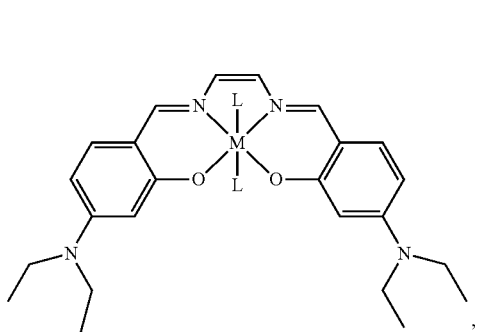

L = MeCN

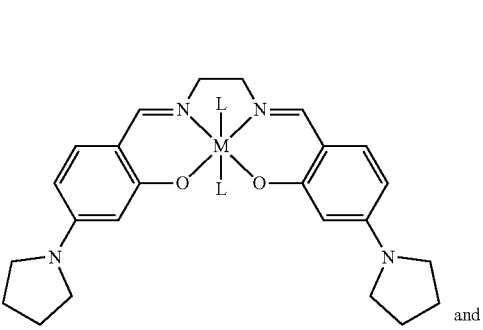

L = MeCN

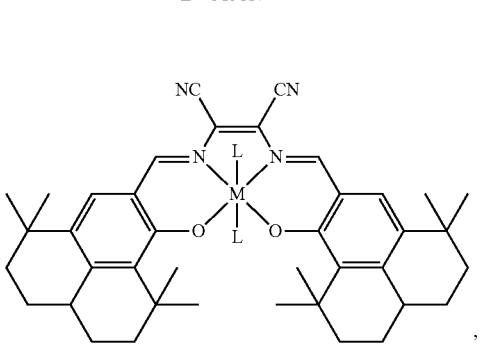

L = MeCN and or pharmaceutically acceptable salt, solvate, non-covalent bond compound or prodrug thereof;

wherein M is a p-block metal.

2. The main group metal compound according to claim 1, wherein M is selected from the group consisting of aluminum, gallium, indium, thallium, germanium, tin and lead.

3. The main group metal compound according to claim 2, wherein the main group metal compound is selected from the group consisting of

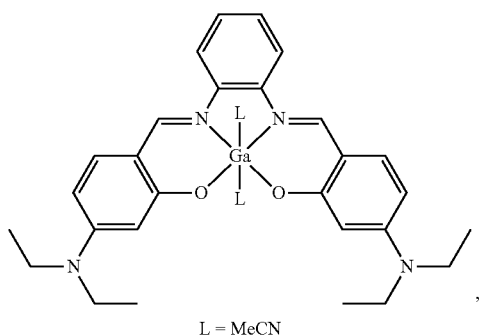
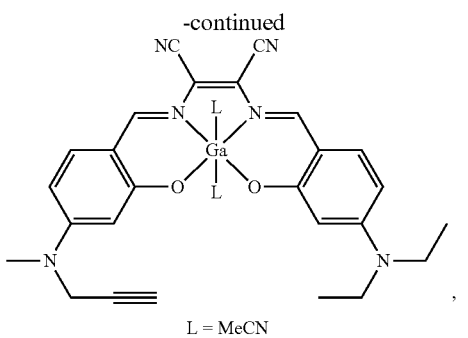
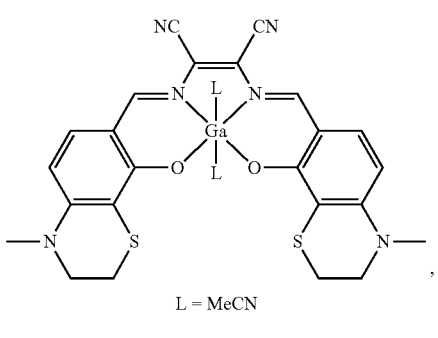
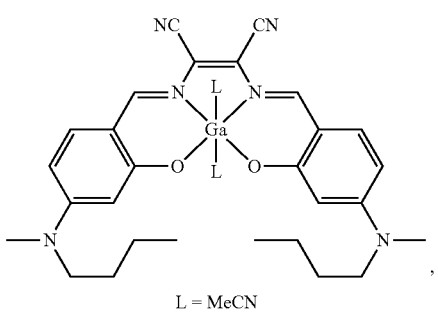
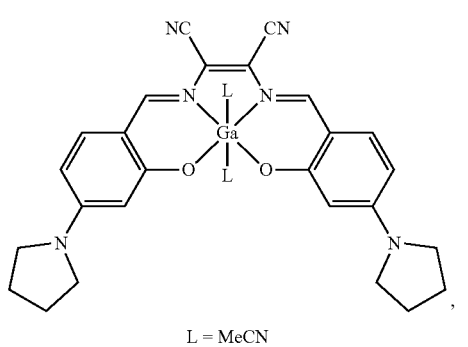
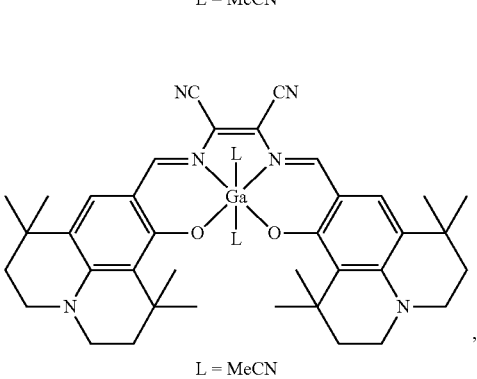

-continued

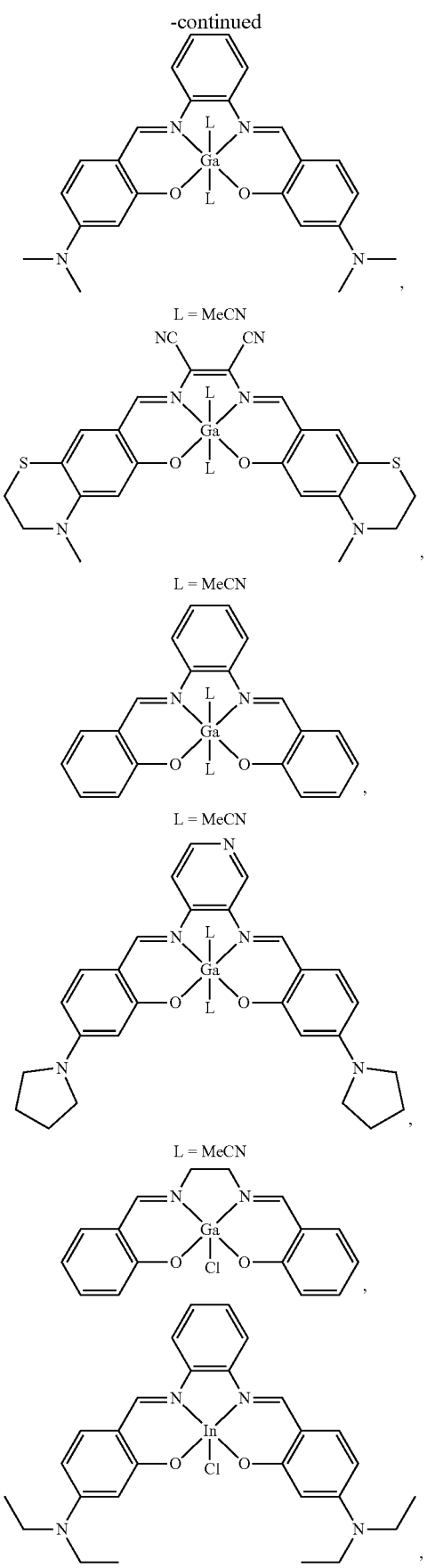

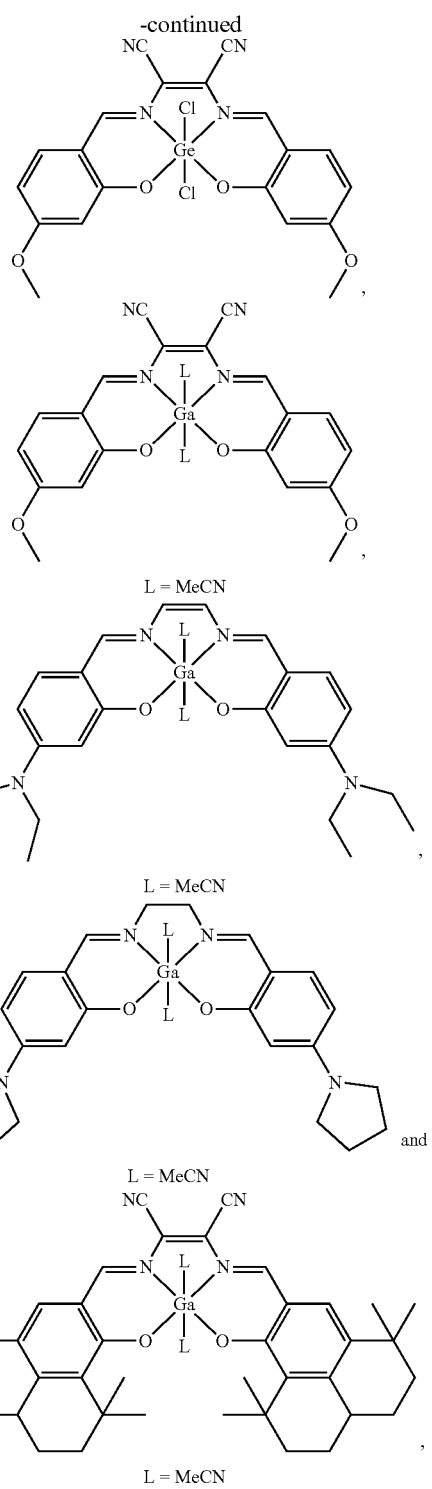

or pharmaceutically acceptable salt, solvate, non-covalent bond compound or prodrug thereof.

4. The main group metal compound according to claim 1, wherein the main group metal compound is conjugated with optical labeling for fluorescence imaging, targeted preparation, administration monitoring, luminescent material, organic light-emitting diode, and dye-sensitized solar cell.

5. A pharmaceutical composition using the main group metal compound according to claim 1 as an active ingredient, comprising pharmaceutically acceptable excipients.

6. The pharmaceutical composition according to claim 5, wherein the pharmaceutical composition is administrated through gastrointestinal tract or by injection,
  wherein the pharmaceutical composition administrated through gastrointestinal tract is prepared in the form of tablet, capsule, oral solution, oral emulsion, suppository or granule; and
  the pharmaceutical composition administrated by injection is prepared in the form of injection solution, injection emulsion, injection sustained-release solution or injection suspension.

7. A method for treating a cancer comprising a step of administrating a subject in need of treatment with the main group metal compound of claim 1.

8. The method according to claim 7, wherein the cancer is selected from the group consisting of breast cancer, liver cancer, lung cancer, melanoma, prostate cancer, colon cancer, colorectal cancer, glioblastoma, kidney cancer, pancreatic cancer, gastric cancer, lymphoma, cervical cancer, ovarian cancer, esophageal cancer, nasal cancer, leukemia, breast duct cancer, gallbladder cancer, testicular cancer, cardia cancer and thyroid cancer.

9. The method according to claim 7, wherein an amount of the main group metal compound for administrating the subject is a daily dosage of 0.01-200 mg/kg body weight of the subject or of 0.5-14 grams.

* * * * *